US007179457B2

(12) United States Patent
Bensi et al.

(10) Patent No.: US 7,179,457 B2
(45) Date of Patent: Feb. 20, 2007

(54) MODIFIED NODAVIRUS RNA FOR GENE DELIVERY

(75) Inventors: Giuliano Bensi, Florence (IT); Alessio Zippo, Bologna (IT)

(73) Assignee: Chiron S.r.l., Siena (IT)

( * ) Notice: Subject to any disclaimer, the term of this patent is extended or adjusted under 35 U.S.C. 154(b) by 590 days.

(21) Appl. No.: 10/221,993

(22) PCT Filed: Mar. 26, 2001

(86) PCT No.: PCT/IB01/00566

§ 371 (c)(1),
(2), (4) Date: Jan. 7, 2003

(87) PCT Pub. No.: WO01/71017

PCT Pub. Date: Sep. 27, 2001

(65) Prior Publication Data
US 2003/0157130 A1    Aug. 21, 2003

(30) Foreign Application Priority Data
Mar. 24, 2000  (GB) .............................. 0007231.4

(51) Int. Cl.
*A01N 63/00*   (2006.01)
(52) U.S. Cl. ............... 424/93.2; 424/93.1; 424/93.6; 435/320.1; 435/455; 435/456; 435/91.1; 435/91.3; 435/91.32; 435/91.33; 536/23.1; 536/23.2; 536/23.4; 536/23.72; 536/24.1
(58) Field of Classification Search ........... 435/320.1, 435/455, 456, 325, 366, 69.1, 91.4, 91.41, 435/91.1, 91.3, 235.1; 536/23.1, 23.72, 24.1
See application file for complete search history.

(56) References Cited

U.S. PATENT DOCUMENTS
6,514,757 B1 * 2/2003 Ball et al. .................. 435/325

FOREIGN PATENT DOCUMENTS
| WO | WO 96/05293 A1 | 2/1996 |
| WO | WO 97/46693 A1 | 12/1997 |
| WO | WO 98/02548 A2 | 1/1998 |
| WO | WO 99/61597 A2 | 12/1999 |
| WO | WO 00/77217 A1 | 12/2000 |

OTHER PUBLICATIONS

Ball et al., "Replication of nodamura virus after transfection of viral RNA into mammalian cells in culture," *J. Virol.* 66:2326-2334, 1992.
Ball, "Cellular expression of a functional nodavirus RNA replicon from vaccinia virus vectors," *J. Virol.* 66:2335-2345, 1992.
Ball, "Requirements for the self-directed replication of flock house virus RNA 1," *J. Virol.* 69:720-727, 1995.
Buratti et al., "Conformational display of two neutralizing epitopes of HIV-1 gp41 on the Flock House virus capsid protein," *J. Immunol. Methods* 197:7-18, 1996.
Chen et al., "An RNA-binding peptide from bovine immunodeficiency virus tat protein recognizes an unusual RNA structure," *Biochemistry* 33:2708-2715, 1994.
Gallagher et al., "Autonomous replication and expression of RNA 1 from black beetle virus," *J. Virol.* 46:481-489, 1983.
Helga-Maria et al., "An intact TAR element and cytoplasmic localization are necessary for efficient packaging of human immunodficiency virus type 1 genomic RNA," *J. Virol.* 73:4127-4135, 1999.
Johnson et al., "Induction and maintenance of autonomous flock house virus RNA1 replication," *J. Virol.* 73:7933-7942, 1999.
Kawana et al., "In vitro construction of pseudovirions of human papillomavirus type 16: incorporation of plasmid DNA into reassembled L1/L2 capsids," *J. Virol.* 72:10298-10300, 1998.
Le Cann et al., "Detection of antibodies against human papillomavirus (HPV) type 16 virions by enzyme-linked immunosorbent assay using recombinant HPV 16 L1 capsids produced by recombinant baculovirus," *J. Clin. Microbiol.* 33:1380-1382, 1995.
Lorenzi et al., "Sequence-specific antibodies against human IgE isoforms induced by an epitope display system," *Immunotechnol.* 4:267-272, 1999.
Müller et al., "Chimeric Papillomavirus-like Particles," *Virol.* 234:93-111, 1997.
Schiappacassi et al., "V3 loop core region serotyping of HIV-1 infected patients using the FHV epitope presenting system," *J. Virol. Methods* 63:121-127, 1997.
Scodeller et al., "A new epitope presenting system displays a HIV-1 V3 loop sequence and induces neutralizing antibodies," *Vaccine* 13:1233-1239, 1995.
Touze et al., "In vitro gene transfer using human papillomavirus-like particles," *Nucl. Acid. Res.* 26:1317-1323, 1998.
Unckell et al., "Generation and neutralization of pseudovirions of human papillomavirus type 33," *J. Virol.* 71:2934-2939, 1997.
Zhao et al., "DNA Packaging by L1 and L2 Capsid Proteins of Bovine Papillomavirus Type 1," *Virol.* 243:482-491, 1998.

* cited by examiner

Primary Examiner—David Guzo
(74) Attorney, Agent, or Firm—Roberta L. Robins; Helen Lee; Alisa A. Harbin

(57) ABSTRACT

The invention provides a nodavirus RNA1 molecule modified to include a heterologous insertion which is downstream of its replicase ORF and, preferably, its B2 ORF. The insertion preferably comprises one or more protein-coding regions. The modified RNA1 may be packaged in a VLP, such as a papillomavirus VLP. The small size of nodavirus RNA1 makes it ideal for HPV packaging.

49 Claims, 26 Drawing Sheets

FIGURE 1

```
         GTTTTCGAAACAAATAAAACAGAAAAGCGAACCTAAACAATGACTCTAAAAGTTATTCTT
    1    ---------+---------+---------+---------+---------+---------+  60
         CAAAAGCTTTGTTTATTTTGTCTTTTCGCTTGGATTTGTTACTGAGATTTTCAATAAGAA a        V  F  E  T  N  K  T  E  K  R  T  *  T  M  T  L  K  V  I  L   -
b         F  S  K  Q  I  K  Q  K  S  E  P  K  Q  *  L  *  K  L  F  L  -

GGAGAACACCAGATCACCCGAACTGAATTGTTAGTCGGGATTGCAACCGTATCTGGGTGC
   61    ---------+---------+---------+---------+---------+---------+  120
         CCTCTTGTGGTCTAGTGGGCTTGACTTAACAATCAGCCCTAACGTTGGCATAGACCCACG a        G  E  H  Q  I  T  R  T  E  L  L  V  G  I  A  T  V  S  G  C   -
b         E  N  T  R  S  P  E  L  N  C  *  S  G  L  Q  P  Y  L  G  A  -

GGTGCCGTAGTGTACTGCATATCCAAGTTCTGGGGCTATGGGGCAATTGCGCCCTATCCT
  121    ---------+---------+---------+---------+---------+---------+ 180
         CCACGGCATCACATGACGTATAGGTTCAAGACCCCGATACCCCGTTAACGCGGGATAGGA a        G  A  V  V  Y  C  I  S  K  F  W  G  Y  G  A  I  A  P  Y  P   -
b         V  P  *  C  T  A  Y  P  S  S  G  A  M  G  Q  L  R  F  I  L  -

CAGAGTGGAGGGAACCGAGTTACACGCGCATTGCAACGGGCTGTCATTGACAAAACGAAG
  181    ---------+---------+---------+---------+---------+---------+ 240
         GTCTCACCTCCCTTGGCTCAATGTGCGCGTAACGTTGCCCGACAGTAACTGTTTTGCTTC a        Q  S  G  G  N  R  V  T  R  A  L  Q  R  A  V  I  D  K  T  K   -
b         R  V  E  G  T  E  L  H  A  H  C  N  G  L  S  L  T  K  R  R  -

ACCCCGATAGAGACACGTTTCTATCCGCTTGACAGCCTGCGTACCGTGACGCCTAAGCGT
  241    ---------+---------+---------+---------+---------+---------+ 300
         TGGGGCTATCTCTGTGCAAAGATAGGCGAACTGTCGGACGCATGGCACTGCGGATTCGCA a        T  P  I  E  T  R  F  Y  P  L  D  S  L  R  T  V  T  P  K  R   -
b         P  R  *  R  H  V  S  I  R  L  T  A  C  V  P  *  R  L  S  V  -

GTCGCAGACAACGGGCACGCCGTTTCAGGGGCCGTACGTGATGCCGCACGTCGTTTGATC
  301    ---------+---------+---------+---------+---------+---------+ 360
         CAGCGTCTGTTGCCCGTGCGGCAAAGTCCCCGGCATGCACTACGGCGTGCAGCAAACTAG a        V  A  D  N  G  H  A  V  S  G  A  V  R  D  A  A  R  R  L  I   -
b         S  Q  T  T  G  T  P  F  Q  G  P  Y  V  M  P  H  V  V  *  S  -

GACGAGTCCATCACGGCCGTTGGAGGATCCAAATTTGAGGTCAACCCCAACCCAAACTCA
  361    ---------+---------+---------+---------+---------+---------+ 420
         CTGCTCAGGTAGTGCCGGCAACCTCCTAGGTTTAAACTCCAGTTGGGGTTGGGTTTGAGT a        D  E  S  I  T  A  V  G  G  S  K  F  E  V  N  P  N  P  N  S   -
b         T  S  P  S  R  P  L  E  D  P  N  L  R  S  T  P  T  Q  T  Q  -

AGCACTGGACTGCGAAACCATTTCCACTTCGCCGTCGGTGATTTGGCACAAGATTTCCGT
  421    ---------+---------+---------+---------+---------+---------+ 480
         TCGTGACCTGACGCTTTGGTAAAGGTGAAGCGGCAGCCACTAAACCGTGTTCTAAAGGCA a        S  T  G  L  R  N  H  F  H  F  A  V  G  D  L  A  Q  D  F  R   -
b         A  L  D  C  E  T  I  S  T  S  P  S  V  I  W  H  K  I  S  V  -

AATGACACACCTGCGGATGATGCCTTCATCGTCGGTGTTGATGTTGATTATTATGTCACC
  481    ---------+---------+---------+---------+---------+---------+ 540
         TTACTGTGTGGACGCCTACTACGGAAGTAGCAGCCACAACTACAACTAATAATACAGTGG a        N  D  T  P  A  D  D  A  F  I  V  G  V  D  V  D  Y  Y  V  T   -
b         M  T  H  L  R  M  M  P  S  S  S  V  L  M  L  I  I  M  S  P  -

GAGCCTGATGTGCTTTTAGAGCACATGCGTCCAGTAGTGTTACACACCTTTAACCCGAAG
  541    ---------+---------+---------+---------+---------+---------+ 600
         CTCGGACTACACGAAAATCTCGTGTACGCAGGTCATCACAATGTGTGGAAATTGGGCTTC a        E  P  D  V  L  L  E  H  M  R  P  V  V  L  H  T  F  N  P  K   -
b         S  L  M  C  F  *  S  T  C  V  Q  *  C  Y  T  P  L  T  R  R  -
```

FIGURE 1 continued...

```
       AAAGTGAGCGGTTTTGATGCTGACTCACCATTCACCATTAAGAACAACTTGGTTGAATAT
   601 ---------+---------+---------+---------+---------+---------+ 660
       TTTCACTCGCCAAAACTACGACTGAGTGGTAAGTGGTAATTCTTGTTGAACCAACTTATA a      K  V  S  G  F  D  A  D  S  P  F  T  I  K  N  N  L  V  E  Y   -
b      K  *  A  V  L  M  L  T  H  H  S  P  L  R  T  T  W  L  N  I   -

AAGGTTAGCGGTGGAGCAGCATGGGTCCATCCAGTTTGGGATTGGTGCGAAGCTGGTGAG
   661 ---------+---------+---------+---------+---------+---------+ 720
       TTCCAATCGCCACCTCGTCGTACCCAGGTAGGTCAAACCCTAACCACGCTTCGACCACTC a      K  V  S  G  G  A  A  W  V  H  P  V  W  D  W  C  E  A  G  E   -
b      R  L  A  V  E  Q  H  G  S  I  Q  F  G  I  G  A  K  L  V  S   -

TTTATCGCTAGCAGAGTCCGTACCAGCTGGAAGGAGTGGTTTTTACAACTACCACTGCGA
   721 ---------+---------+---------+---------+---------+---------+ 780
       AAATAGCGATCGTCTCAGGCATGGTCGACCTTCCTCACCAAAAATGTTGATGGTGACGCT a      F  I  A  S  R  V  R  T  S  W  K  E  W  F  L  Q  L  P  L  R   -
b      L  S  L  A  E  S  V  P  A  G  R  S  G  F  Y  N  Y  H  C  E   -

ATGATTGGTTTGGAGAAGGTTGGCTATCATAAAATCCATCATTGTAGACCGTGGACTGAT
   781 ---------+---------+---------+---------+---------+---------+ 840
       TACTAACCAAACCTCTTCCAACCGATAGTATTTTAGGTAGTAACATCTGGCACCTGACTA a      M  I  G  L  E  K  V  G  Y  H  K  I  H  H  C  R  P  W  T  D   -
b      *  L  V  W  R  R  L  A  I  I  K  S  I  I  V  D  R  G  L  I   -

TGTCCAGATCGTGCACTTGTCTACACTATACCGCAATATGTCATTTGGCGATTTAATTGG
   841 ---------+---------+---------+---------+---------+---------+ 900
       ACAGGTCTAGCACGTGAACAGATGTGATATGGCGTTATACAGTAAACCGCTAAATTAACC a      C  P  D  R  A  L  V  Y  T  I  P  Q  Y  V  I  W  R  F  N  W   -
b      V  Q  I  V  H  L  S  T  L  Y  R  N  M  S  F  G  D  L  I  G   -

ATTGATACCGAACTACACGTGCGAAAACTGAAACGGATTGAATACCAGGACGAAACCAAA
   901 ---------+---------+---------+---------+---------+---------+ 960
       TAACTATGGCTTGATGTGCACGCTTTTGACTTTGCCTAACTTATGGTCCTGCTTTGGTTT a      I  D  T  E  L  H  V  R  K  L  K  R  I  E  Y  Q  D  E  T  K   -
b      L  I  P  N  Y  T  C  E  N  *  N  G  L  N  T  R  T  K  P  N   -

CCTGGTTGGAACAGATTGGAGTATGTGACCGACAAGAATGAACTGCTGGTTTCCATCGGT
   961 ---------+---------+---------+---------+---------+---------+ 1020
       GGACCAACCTTGTCTAACCTCATACACTGGCTGTTCTTACTTGACGACCAAAGGTAGCCA a      P  G  W  N  R  L  E  Y  V  T  D  K  N  E  L  L  V  S  I  G   -
b      L  V  G  T  D  W  S  M  *  P  T  R  M  N  C  W  F  P  S  V   -

CGAGAAGGGGAGCATGCTCAGATTACTATCGAGAAAGAAAAGTTGGATATGCTCTCGGGA
  1021 ---------+---------+---------+---------+---------+---------+ 1080
       GCTCTTCCCCTCGTACGAGTCTAATGATAGCTCTTTCTTTTCAACCTATACGAGAGCCCT a      R  E  G  E  H  A  Q  I  T  I  E  K  E  K  L  D  M  L  S  G   -
b      E  K  G  S  M  L  R  L  L  S  R  K  K  S  W  I  C  S  R  D   -

TTATCCGCCACCCAATCTGTCAACGCTAGGCTTATCGGTATGGGACACAAGGACCCGCAA
  1081 ---------+---------+---------+---------+---------+---------+ 1140
       AATAGGCGGTGGGTTAGACAGTTGCGATCCGAATAGCCATACCCTGTGTTCCTGGGCGTT a      L  S  A  T  Q  S  V  N  A  R  L  I  G  M  G  H  K  D  P  Q   -
b      Y  P  P  P  N  L  S  T  L  G  L  S  V  W  D  T  R  T  R  N   -

TACACATCCATGATTGTCCAGTATTATACTGGCAAGAAGGTAGTGTCACCAATTAGTCCA
  1141 ---------+---------+---------+---------+---------+---------+ 1200
       ATGTGTAGGTACTAACAGGTCATAATATGACCGTTCTTCCATCACAGTGGTTAATCAGGT a      Y  T  S  M  I  V  Q  Y  Y  T  G  K  K  V  V  S  P  I  S  P   -
b      T  H  P  *  L  S  S  I  I  L  A  R  R  *  C  H  Q  L  V  Q   -
```

FIGURE 1 continued...

```
              ACTGTGTATAAACCTACAATGCCACGCGTCCATTGGCCAGTAACCAGTGACGCAGATGTA
      1201  ---------+---------+---------+---------+---------+---------+ 1260
              TGACACATATTTGGATGTTACGGTGCGCAGGTAACCGGTCATTGGTCACTGCGTCTACAT a           T  V  Y  K  P  T  M  P  R  V  H  W  P  V  T  S  D  A  D  V  -
  b             L  C  I  N  L  Q  C  H  A  S  I  G  Q  *  P  V  T  Q  M  Y  -

CCAGAAGTGAGCGCGCGCCAATACACACTGCCTATCGTGAGTGACTGTATGATGATGCCA
      1261  ---------+---------+---------+---------+---------+---------+ 1320
              GGTCTTCACTCGCGCGCGGTTATGTGTGACGGATAGCACTCACTGACATACTACTACGGT a           P  E  V  S  A  R  Q  Y  T  L  P  I  V  S  D  C  M  M  M  P  -
  b             Q  K  *  A  R  A  N  T  H  C  L  S  *  V  T  V  *  *  C  Q  -

ATGATCAAGCGCTGGGAAACAATGTCTGAATCAATTGAACGTAGGGTGACTTTTGTCGCC
      1321  ---------+---------+---------+---------+---------+---------+ 1380
              TACTAGTTCGCGACCCTTTGTTACAGACTTAGTTAACTTGCATCCCACTGAAAACAGCGG a           M  I  K  R  W  E  T  M  S  E  S  I  E  R  R  V  T  F  V  A  -
  b             *  S  S  A  G  K  Q  C  L  N  Q  L  N  V  G  *  L  L  S  P  -

AATGATAAGAAACCAAGCGACAGAATCGCCAAAATAGCCGAAACGTTTGTTAAATTGATG
      1381  ---------+---------+---------+---------+---------+---------+ 1440
              TTACTATTCTTTGGTTCGCTGTCTTAGCGGTTTTATCGGCTTTGCAAACAATTTAACTAC a           N  D  K  K  P  S  D  R  I  A  K  I  A  E  T  F  V  K  L  M  -
  b             M  I  R  N  Q  A  T  E  S  P  K  *  P  K  R  L  L  N  *  *  -

AATGGGCCATTCAAAGATCTTGACCCTTTGTCGATTGAAGAAACGATTGAACGGCTGAAT
      1441  ---------+---------+---------+---------+---------+---------+ 1500
              TTACCCGGTAAGTTTCTAGAACTGGGAAACAGCTAACTTCTTTGCTAACTTGCCGACTTA a           N  G  P  F  K  D  L  D  P  L  S  I  E  E  T  I  E  R  L  N  -
  b             M  G  H  S  K  I  L  T  L  C  R  L  K  K  R  L  N  G  *  I  -

AAACCGTCCCAACAATTACAACTTAGGGCGGTTTTCGAAATGATTGGAGTTAAACCTCGT
      1501  ---------+---------+---------+---------+---------+---------+ 1560
              TTTGGCAGGGTTGTTAATGTTGAATCCCGCCAAAAGCTTTACTAACCTCAATTTGGAGCA a           K  P  S  Q  Q  L  Q  L  R  A  V  F  E  M  I  G  V  K  P  R  -
  b             N  R  P  N  N  Y  N  L  G  R  F  S  K  *  L  E  L  N  L  V  -

CAATTGATTGAGTCGTTCAACAAGAACGAACCTGGAATGAAATCTAGCCGGATAATATCC
      1561  ---------+---------+---------+---------+---------+---------+ 1620
              GTTAACTAACTCAGCAAGTTGTTCTTGCTTGGACCTTACTTTAGATCGGCCTATTATAGG a           Q  L  I  E  S  F  N  K  N  E  P  G  M  K  S  S  R  I  I  S  -
  b             N  *  L  S  R  S  T  R  T  N  L  E  *  N  L  A  G  *  Y  P  -

GGTTTTCCAGACATACTTTTCATCTTGAAAGTTTCCAGATACACCTTAGCGTATTCGGAT
      1621  ---------+---------+---------+---------+---------+---------+ 1680
              CCAAAAGGTCTGTATGAAAAGTAGAACTTTCAAAGGTCTATGTGGAATCGCATAAGCCTA a           G  F  P  D  I  L  F  I  L  K  V  S  R  Y  T  L  A  Y  S  D  -
  b             V  F  Q  T  Y  F  S  S  *  K  F  P  D  T  P  *  R  I  R  I  -

ATAGTTCTACATGCCGAACACAATGAACATTGGTATTACCCCGGGCGGAACCCGACTGAG
      1681  ---------+---------+---------+---------+---------+---------+ 1740
              TATCAAGATGTACGGCTTGTGTTACTTGTAACCATAATGGGGCCCGCCTTGGGCTGACTC a           I  V  L  H  A  E  H  N  E  H  W  Y  Y  P  G  R  N  P  T  E  -
  b             *  F  Y  M  P  N  T  M  N  I  G  I  T  P  G  G  T  R  L  R  -

ATCGCCGACGGTGTTTGTGAGTTTGTTAGTGACTGTGATGCTGAAGTCATAGAAACTGAC
      1741  ---------+---------+---------+---------+---------+---------+ 1800
              TAGCGGCTGCCACAAACACTCAAACAATCACTGACACTACGACTTCAGTATCTTTGACTG a           I  A  D  G  V  C  E  F  V  S  D  C  D  A  E  V  I  E  T  D  -
  b             S  P  T  V  F  V  S  L  L  V  T  V  M  L  K  S  *  K  L  T  -
```

FIGURE 1 continued...

```
       TTCTCCAACCTCGATGGCAGGGTTTCCAGCTGGATGCAAAGAAACATCGCCCAAAAGGCC
  1801 ---------+---------+---------+---------+---------+---------+ 1860
       AAGAGGTTGGAGCTACCGTCCCAAAGGTCGACCTACGTTTCTTTGTAGCGGGTTTTCCGG a      F  S  N  L  D  G  R  V  S  S  W  M  Q  R  N  I  A  Q  K  A   -
b         S  P  T  S  M  A  G  F  P  A  G  C  K  E  T  S  P  K  R  P -

ATGGTTCAAGCATTCCGCCCAGAATACAGAGATGAGATCATTTCATTCATGGACACGATA
  1861 ---------+---------+---------+---------+---------+---------+ 1920
       TACCAAGTTCGTAAGGCGGGTCTTATGTCTCTACTCTAGTAAAGTAAGTACCTGTGCTAT a      M  V  Q  A  F  R  P  E  Y  R  D  E  I  I  S  F  M  D  T  I   -
b         W  F  K  H  S  A  Q  N  T  E  M  R  S  F  H  S  W  T  R  * -

ATCAATTGTCCAGCTAAAGCTAAACGCTTTGGTTTCCGATATGAGCCTGGTGTAGGCGTT
  1921 ---------+---------+---------+---------+---------+---------+ 1980
       TAGTTAACAGGTCGATTTCGATTTGCGAAACCAAAGGCTATACTCGGACCACATCCGCAA a      I  N  C  P  A  K  A  K  R  F  G  F  R  Y  E  P  G  V  G  V   -
b         S  I  V  Q  L  K  L  N  A  L  V  S  D  M  S  L  V  A  L   -

AAAAGTGGAAGTCCAACAACCACGCCACATAACACCCAATACAATGGATGTGTCGAATTT
  1981 ---------+---------+---------+---------+---------+---------+ 2040
       TTTTCACCTTCAGGTTGTTGGTGCGGTGTATTGTGGGTTATGTTACCTACACAGCTTAAA a      K  S  G  S  P  T  T  T  P  H  N  T  Q  Y  N  G  C  V  E  F   -
b         K  V  E  V  Q  Q  P  R  H  I  T  P  N  T  M  D  V  S  N  L -

ACAGCTCTGACCTTTGAGCATCCTGATGCTGAACCTGAAGATTTGTTCCGTTTAATCGGA
  2041 ---------+---------+---------+---------+---------+---------+ 2100
       TGTCGAGACTGGAAACTCGTAGGACTACGACTTGGACTTCTAAACAAGGCAAATTAGCCT a      T  A  ·L  T  F  E  H  P  D  A  E  P  E  D  L  F  R  L  I  G  -
b         Q  L  *  P  L  S  I  L  M  L  N  L  K  I  C  S  V  *  S  D -

CCGAAGTGCGGTGATGATGGTCTTTCCCGGGCTATCATTCAAAAATCAATTAATCGCGCT
  2101 ---------+---------+---------+---------+---------+---------+ 2160
       GGCTTCACGCCACTACTACCAGAAAGGGCCCGATAGTAAGTTTTTAGTTAATTAGCGCGA a      P  K  C  G  D  D  G  L  S  R  A  I  I  Q  K  S  I  N  R  A   -
b         R  S  A  V  M  M  V  F  P  G  L  S  F  K  N  Q  L  I  A  L -

GCCAAGTGTTTCGGCCTCGAACTCAAAGTTGAACGATACAATCCAGAGATAGGTCTTTGT
  2161 ---------+---------+---------+---------+---------+---------+ 2220
       CGGTTCACAAAGCCGGAGCTTGAGTTTCAACTTGCTATGTTAGGTCTCTATCCAGAAACA a      A  K  C  F  G  L  E  L  K  V  E  R  Y  N  P  E  I  G  L  C   -
b         P  S  V  S  A  S  N  S  K  L  N  D  T  I  Q  R  *  V  F  V -

TTCCTGTCTCGTGTATTTGTGGACCCGCTCGCAACTACGACCACAATTCAAGACCCACTG
  2221 ---------+---------+---------+---------+---------+---------+ 2280
       AAGGACAGAGCACATAAACACCTGGGCGAGCGTTGATGCTGGTGTTAAGTTCTGGGTGAC a      F  L  S  R  V  F  V  D  P  L  A  T  T  T  T  I  Q  D  P  L   -
b         S  C  L  V  Y  L  W  T  R  S  Q  L  R  P  Q  F  K  T  H  C -

CGTACTCTGCGAAAACTACATCTTACAACAAGAGATCCAACGATACCATTAGCTGATGCG
  2281 ---------+---------+---------+---------+---------+---------+ 2340
       GCATGAGACGCTTTTGATGTAGAATGTTGTTCTCTAGGTTGCTATGGTAATCGACTACGC a      R  T  L  R  K  L  H  L  T  T  R  D  P  T  I  P  L  A  D  A   -
b         V  L  C  E  N  Y  I  L  Q  Q  E  I  Q  R  Y  H  *  L  M  R -

GCTTGCGACCGTGTCGAAGGCTATCTCTGTACCGATGCGCTTACTCCGTTAATTTCGGAT
  2341 ---------+---------+---------+---------+---------+---------+ 2400
       CGAACGCTGGCACAGCTTCCGATAGAGACATGGCTACGCGAATGAGGCAATTAAAGCCTA a      A  C  D  R  V  E  G  Y  L  C  T  D  A  L  T  P  L  I  S  D   -
b         L  A  T  V  S  K  A  I  S  V  P  M  R  L  L  R  *  F  R  I -
```

FIGURE 1 continued...

```
       TATTGCAAAATGGTACTACGACTCTACGGGCCCACTGCTTCAACTGAGCAGGTGAGGAAC
  2401 ---------+---------+---------+---------+---------+---------+ 2460
       ATAACGTTTTACCATGATGCTGAGATGCCCGGGTGACGAAGTTGACTCGTCCACTCCTTG a       Y  C  K  M  V  L  R  L  Y  G  P  T  A  S  T  E  Q  V  R  N   -
b         I  A  K  W  Y  Y  D  S  T  G  P  L  L  Q  L  S  R  *  G  T -

CAACGTAGAAGCCGGAATAAAGAGAAGCCCTACTGGTTGACTTGTGACGGATCATGGCA
  2461 ---------+---------+---------+---------+---------+---------+ 2521
       GTTGCATCTTCGGCCTTATTTCTCTTCGGGATGACCAACTGAACACTGCCTAGTACCGGT a       Q  R  R  S  R  N  K  E  K  P  Y  W  L  T  C  D  G  S  W  P   -
b         N  V  E  A  G  I  K  R  S  P  T  G  *  L  V  T  D  H  G  H -

CAGCATCCGCAAGACGCCCATTTGATGAAGCAGGTTTTAATCAAACGTACAGCCATTGAC
  2521 ---------+---------+---------+---------+---------+---------+ 2580
       GTCGTAGGCGTTCTGCGGGTAAACTACTTCGTCCAAAATTAGTTTGCATGTCGGTAACTG a       Q  H  P  Q  D  A  H  L  M  K  Q  V  L  I  K  R  T  A  I  D   -
b         S  I  R  K  T  P  I  *  *  S  R  F  *  S  N  V  Q  P  L  T -

GAAGATCAGGTCGATGCACTCATTGGGCGTTTTGCGGCAATGAAGGATGTCTGGGAGAAA
  2581 ---------+---------+---------+---------+---------+---------+ 2640
       CTTCTAGTCCAGCTACGTGAGTAACCCGCAAAACGCCGTTACTTCCTACAGACCCTCTTT a       E  D  Q  V  D  A  L  I  G  R  F  A  A  M  K  D  V  W  E  K   -
b         K  I  R  S  M  H  S  L  G  V  L  P  Q  *  R  M  S  G  R  K -

ATTACACATGACAGCGAGGAGAGCGCCGCTGCGTGTACGTTTGATGAAGACGGCGTTGCG
  2641 ---------+---------+---------+---------+---------+---------+ 2700
       TAATGTGTACTGTCGCTCCTCTCGCGGCGACGCACATGCAAACTACTTCTGCCGCAACGC a       I  T  H  D  S  E  E  S  A  A  A  C  T  F  D  E  D  G  V  A   -
b         L  H  M  T  A  R  R  A  P  L  R  V  R  L  M  K  T  A  L  R -

CCGAACTCCGTGGACGAATCGTTACCAATGTTAAACGATGCCAAGCAAACTCGCGCTAAT
  2701 ---------+---------+---------+---------+---------+---------+ 2760
       GGCTTGAGGCACCTGCTTAGCAATGGTTACAATTTGCTACGGTTCGTTTGAGCGCGATTA a       P  N  S  V  D  E  S  L  P  M  L  N  D  A  K  Q  T  R  A  N   -
b         R  T  P  W  T  N  R  Y  Q  C  *  T  M  P  S  K  L  A  L  I -

CCAGGAACTTCCCGACCGCATTCAAACGGCGGTGGAAGCAGCCATGGGAATGAGCTACCA
  2761 ---------+---------+---------+---------+---------+---------+ 2820
       GGTCCTTGAAGGGCTGGCGTAAGTTTGCCGCCACCTTCGTCGGTACCCTTACTCGATGGT a       P  G  T  S  R  P  H  S  N  G  G  G  S  S  H  G  N  E  L  P   -
b         Q  E  L  P  D  R  I  Q  T  A  V  E  A  A  M  G  M  S  Y  Q -

AGACGCACCGAACAACGTGCGCAGGGACCTCGACAACCTGCACGCTTGCCTAAACAAGGC
  2821 ---------+---------+---------+---------+---------+---------+ 2880
       TCTGCGTGGCTTGTTGCACGCGTCCCTGGAGCTGTTGGACGTGCGAACGGATTTGTTCCG a       R  R  T  E  Q  R  A  Q  G  P  R  Q  P  A  R  L  P  K  Q  G   -
b         D  A  P  N  N  V  R  R  D  L  D  N  L  H  A  C  L  N  K  A -

AAAACTAACGGTAAGTCGGATGGTAACATCACTGCTGGAGAAACCCAGCGTGGTGGCATA
  2881 ---------+---------+---------+---------+---------+---------+ 2940
       TTTTGATTGCCATTCAGCCTACCATTGTAGTGACGACCTCTTTGGGTCGCACCACCGTAT a       K  T  N  G  K  S  D  G  N  I  T  A  G  E  T  Q  R  G  G  I   -
b         K  L  T  V  S  R  M  V  T  S  L  L  E  K  P  S  V  V  A  Y -

CCTAGAGGGAAAGGCCCCCGAGGAGGCAAAACCAACACTCGAAGAACGCCTCCGAAAGCT
  2941 ---------+---------+---------+---------+---------+---------+ 3000
       GGATCTCCCTTTCCGGGGGCTCCTCCGTTTTGGTTGTGAGCTTCTTGCGGAGGCTTTCGA a       P  R  G  K  G  P  R  G  G  K  T  N  T  R  R  T  P  P  K  A   -
b         L  E  G  K  A  P  E  E  A  K  P  T  L  E  E  R  L  R  K  L -
```

FIGURE 1 continued...

```
       GGAGCTCAGCCACAGCCTTCCAACAACCGGAAGTGACCCCCCACCCGCAAAACTGTAGGT
  3001 ------------+----------+----------+----------+----------+---------+ 3060
       CCTCGAGTCGGTGTCGGAAGGTTGTTGGCCTTCACTGGGGGGTGGGCGTTTTGACATCCA a      G  A  Q  P  Q  P  S  N  N  R  K  *  P  P  T  R  K  T  V  G   -
  b       E  L  S  H  S  L  P  T  T  G  S  D  P  P  P  A  K  L  *  V  -

GGCTCTTAGGAGCACCCACACCCGTTCTAGCCCGAAAGGGCAGAGGT
  3061 ------------+----------+----------+----------+-------- 3107
       CCGAGAATCCTCGTGGGTGTGGGCAAGATCGGGCTTTCCCGTCTCCA a      G  S  *  E  H  P  H  P  F  *  P  E  R  A  E    -
  b       A  L  R  S  T  H  T  R  S  S  P  K  G  Q  R   -
```

FIGURE 2

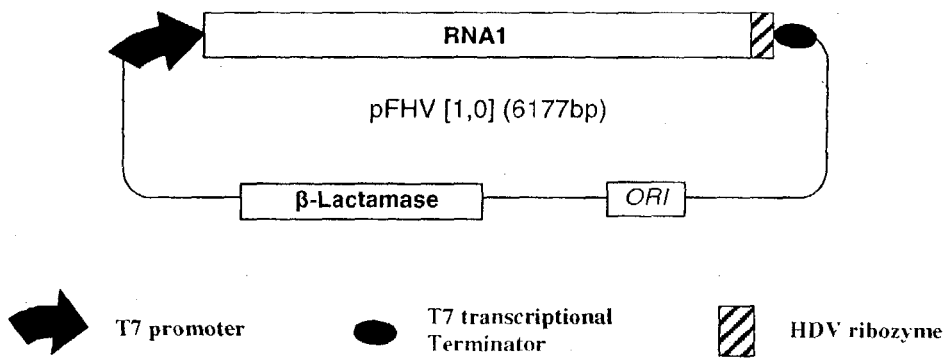

FIGURE 3

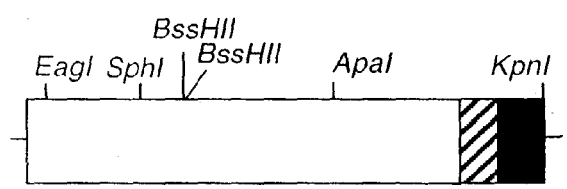

FIGURE 4

```
                       2 BssHII sites
                      ┌────┬────┐
                      │    │    │
Original sequence   3'-... CATTCGCGCGCGGTTA...-5'

Mutated sequence    3'-...CATTCACGCGCGGTTA....-5'   (Reverse Primer)
                         └────────┘
                          1 BssHII site
```

FIGURE 6
(6A)
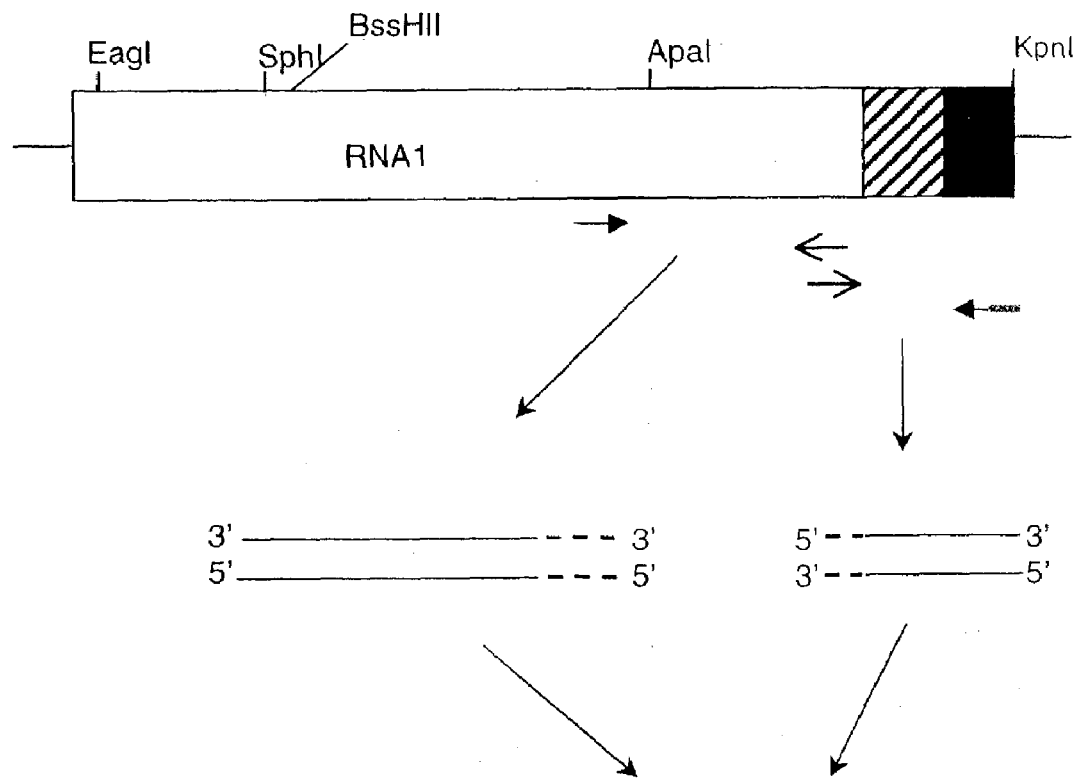
(6B)
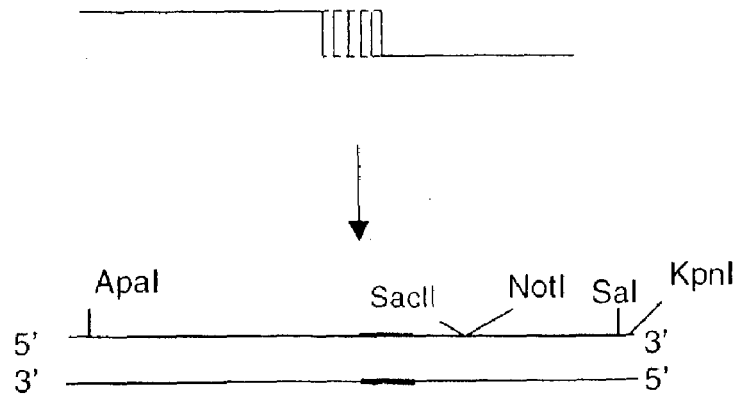

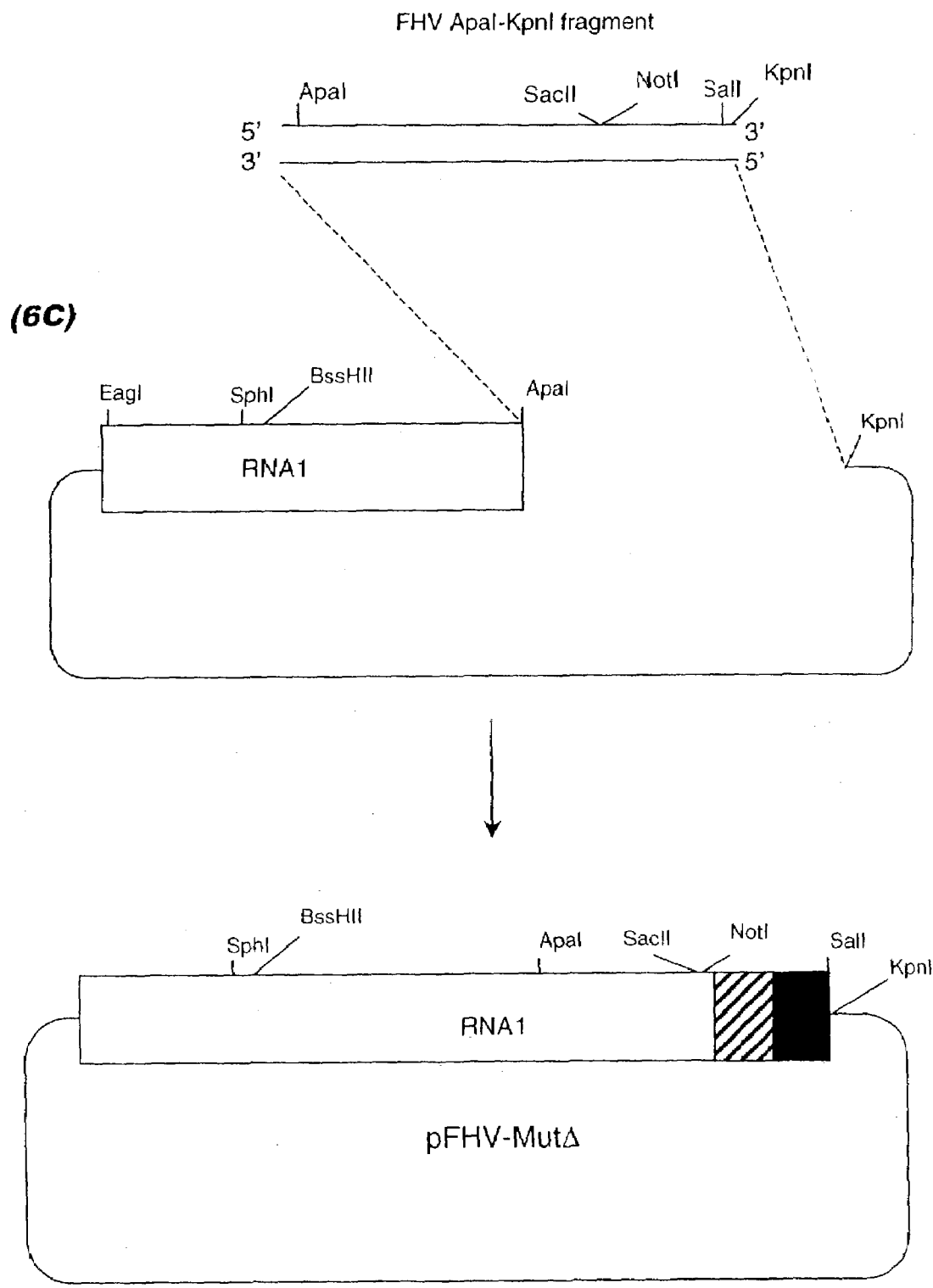

FIGURE 7
(7A) Amplification ADH₂ promoter
→ primer ADH/SAC
← primer P-R1-rev
(7B) Amplification RNA1/SphI
→ primer RNA1-for
→ primer RNA1-r
pSK-ADH₂/6L1 (4966) bp
pFHV (6177bp)
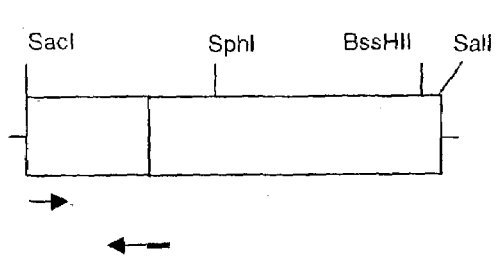
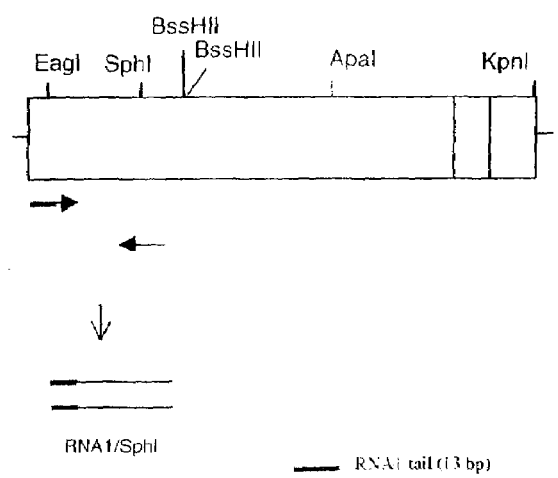
(7C)
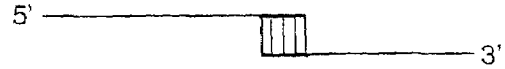
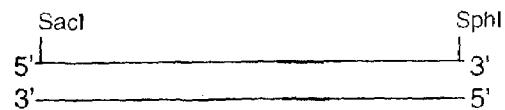

(7D)
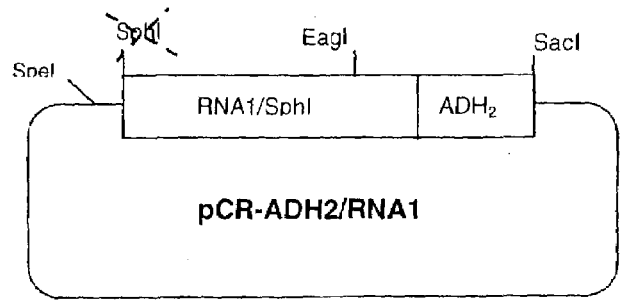
(7E)
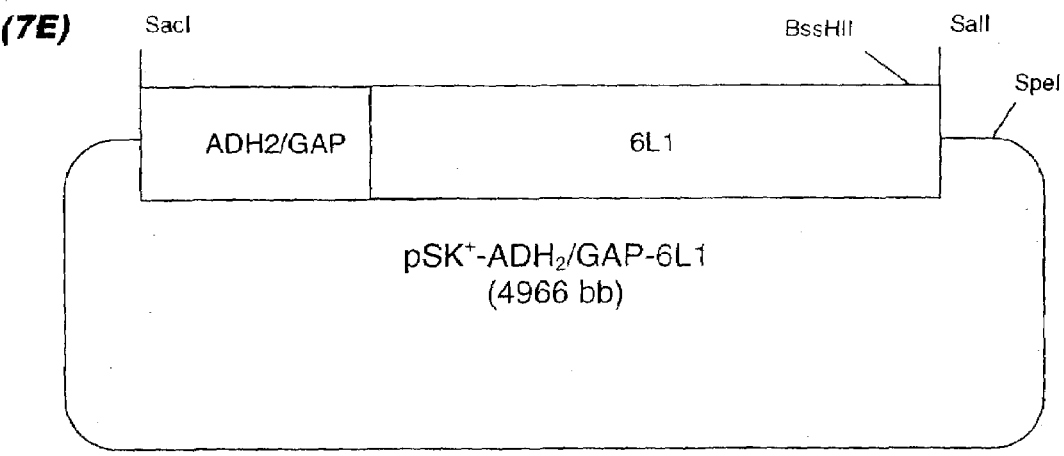
(7F)
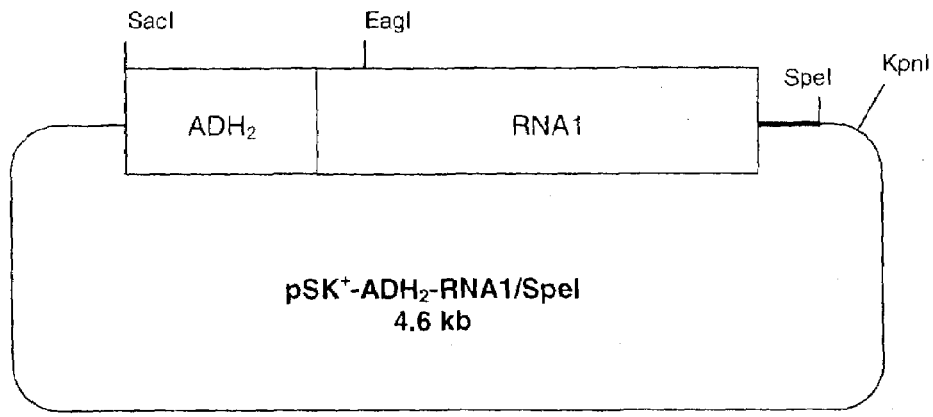

pFHV-εGFP-1/TAR
6987bp pFHV-εGFP-1/TARΔ
6987bp

FIGURE 21
*(21A)*
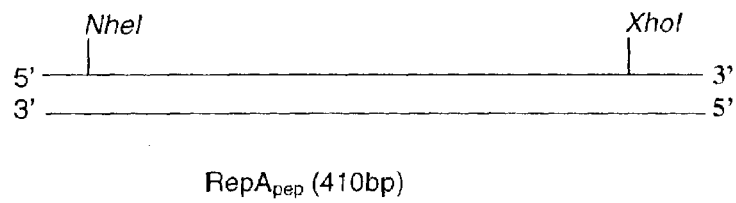
RepA_pep (410bp)
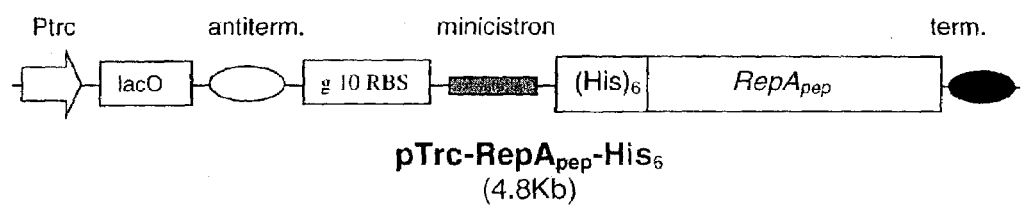
pTrc-RepA_pep-His_6
(4.8Kb)
*(21B)*
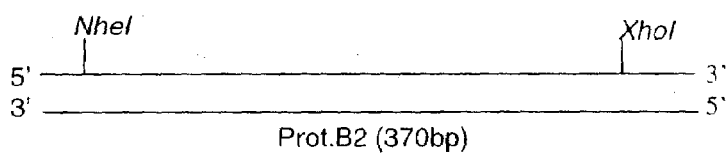
Prot.B2 (370bp)
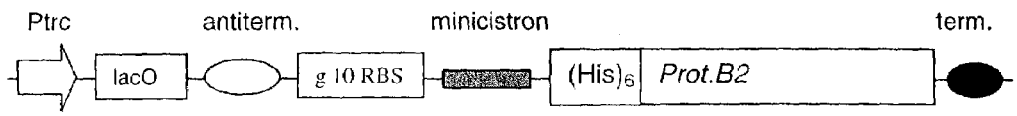
pTrc-B2-His_6
(4.7Kb)

FIGURE 22
(22A)
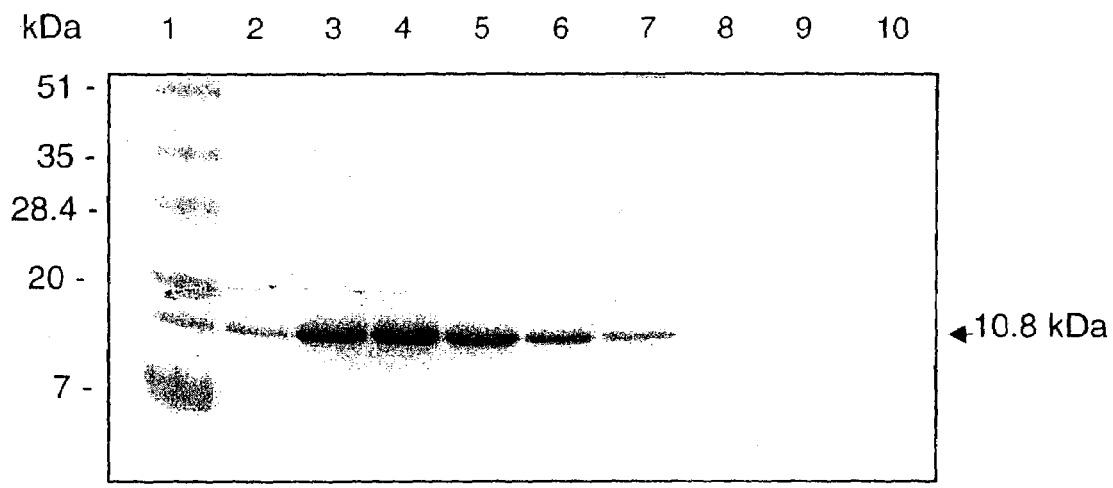
(22B)
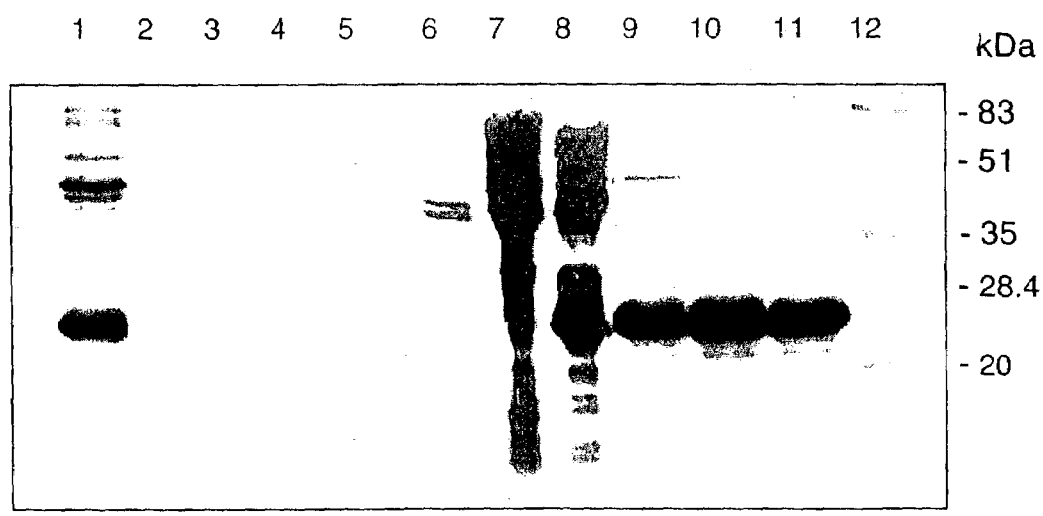

pBS-ADH$_2$/GAP-6L1Δ4-Tat

5' RNA1     GTTTTCGAAACAAATAAAACAG............

35A  35B  35C

SEQUENCE LISTING

<160> NUMBER OF SEQ ID NOS: 36

<210> SEQ ID NO 1
<211> LENGTH: 10
<212> TYPE: PRT
<213> ORGANISM: Artificial Sequence
<220> FEATURE:
<223> OTHER INFORMATION: RepApep replicase

<400> SEQUENCE: 1

Asp Val Trp Glu Lys Ser Asn Asn Arg Lys
1               5                   10

<210> SEQ ID NO 2
<211> LENGTH: 29
<212> TYPE: DNA
<213> ORGANISM: Artificial Sequence
<220> FEATURE:
<223> OTHER INFORMATION: PCR Primer

<400> SEQUENCE: 2
cccaattcgt cttcagagct cattgtttg                                    29

<210> SEQ ID NO 3
<211> LENGTH: 47
<212> TYPE: DNA
<213> ORGANISM: Artificial Sequence
<220> FEATURE:
<223> OTHER INFORMATION: PCR Primer

<400> SEQUENCE: 3
ttgtttcgaa aactagattt acagaattac aatcaatacc taccgtc                47

<210> SEQ ID NO 4
<211> LENGTH: 33
<212> TYPE: DNA
<213> ORGANISM: Artificial Sequence
<220> FEATURE:
<223> OTHER INFORMATION: PCR Primer

<400> SEQUENCE: 4
gttttcgaaa caaataaaac agaaaagcga aac                               33

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
tgagcatgct cccttctcg acc                                           23

<210> SEQ ID NO 6
<211> LENGTH: 92
<212> TYPE: DNA
<213> ORGANISM: Artificial Sequence
<220> FEATURE:
<223> OTHER INFORMATION: PCR Primer

<400> SEQUENCE: 6
gtacaagtaa ggttaccgct agcgggtctc tctggttaga ccagatctga gcctgggagc  60
tctctggcta actagggaac ccactgctta gc                                92

<210> SEQ ID NO 7
<211> LENGTH: 92
<212> TYPE: DNA
<213> ORGANISM: Artificial Sequence
<220> FEATURE:
<223> OTHER INFORMATION: PCR Primer

<400> SEQUENCE: 7
ggccgctaag cagtgggttc cctagttagc cagagagctc ccaggctcag atctggtcta      60
accagagaga cccgctagcg gtaaccttac tt      92

<210> SEQ ID NO 8
<211> LENGTH: 62
<212> TYPE: DNA
<213> ORGANISM: Artificial Sequence
<220> FEATURE:
<223> OTHER INFORMATION: PCR Primer

<400> SEQUENCE: 8
cccacccgca aaactgtagg tgccgcggag gagcggccgc acccgttcta gcccgaaagg      60
gc      62

<210> SEQ ID NO 9
<211> LENGTH: 62
<212> TYPE: DNA
<213> ORGANISM: Artificial Sequence
<220> FEATURE:
<223> OTHER INFORMATION: PCR Primer

<400> SEQUENCE: 9 gcccttcgg gctagaacgg gtgcggccgc tcctccgcgg cacctacagt tttgcgggtg      60
gg      62

<210> SEQ ID NO 10
<211> LENGTH: 24
<212> TYPE: DNA
<213> ORGANISM: Artificial Sequence
<220> FEATURE:
<223> OTHER INFORMATION: PCR Primer

<400> SEQUENCE: 10
ccgtgtcgaa ggctatctct gtac      24

<210> SEQ ID NO 11
<211> LENGTH: 57
<212> TYPE: DNA
<213> ORGANISM: Artificial Sequence
<220> FEATURE:
<223> OTHER INFORMATION: PCR Primer

<400> SEQUENCE: 11
acggaattaa ttcgagctcg gtacccgtcg acctcgatcc ggatatagtt cctcctt      57

<210> SEQ ID NO 12
<211> LENGTH: 25
<212> TYPE: DNA
<213> ORGANISM: Artificial Sequence
<220> FEATURE:
<223> OTHER INFORMATION: PCR Primer

<400> SEQUENCE: 12
ggattgatac cgaactacac gtgcg      25

```
<210> SEQ ID NO 13
<211> LENGTH: 25
<212> TYPE: DNA
<213> ORGANISM: Artificial Sequence
<220> FEATURE:
<223> OTHER INFORMATION: PCR Primer

<400> SEQUENCE: 13
tattggcgcg cactcacttc tggta                                          25

<210> SEQ ID NO 14
<211> LENGTH: 42
<212> TYPE: DNA
<213> ORGANISM: Artificial Sequence
<220> FEATURE:
<223> OTHER INFORMATION: PCR Primer

<400> SEQUENCE: 14
acgttagcta gcgatgtctg ggagaaaatt acacatgaca gc                       42

<210> SEQ ID NO 15
<211> LENGTH: 36
<212> TYPE: DNA
<213> ORGANISM: Artificial Sequence
<220> FEATURE:
<223> OTHER INFORMATION: PCR Primer

<400> SEQUENCE: 15
taacgtctcg agtcacttcc ggttgttgga aggctg                              36

<210> SEQ ID NO 16
<211> LENGTH: 48
<212> TYPE: DNA
<213> ORGANISM: Artificial Sequence
<220> FEATURE:
<223> OTHER INFORMATION: PCR Primer

<400> SEQUENCE: 16
ggccgcactc gaggctcgtg tagctcatta gctccgagcg gtcaccgc                 48

<210> SEQ ID NO 17
<211> LENGTH: 48
<212> TYPE: DNA
<213> ORGANISM: Artificial Sequence
<220> FEATURE:
<223> OTHER INFORMATION: PCR Primer

<400> SEQUENCE: 17
ggccgcggtg accgctcgga gctaatgagc tacacgagcc tcgagtgc                 48

<210> SEQ ID NO 18
<211> LENGTH: 36
<212> TYPE: DNA
<213> ORGANISM: Artificial Sequence
<220> FEATURE:
<223> OTHER INFORMATION: PCR Primer

<400> SEQUENCE: 18
acgttagcta gcccaagcaa actcgcgcta atccag                              36

<210> SEQ ID NO 19
<211> LENGTH: 33
<212> TYPE: DNA
<213> ORGANISM: Artificial Sequence
<220> FEATURE:
<223> OTHER INFORMATION: PCR Primer
```

<400> SEQUENCE: 19
taacgtctcg agctacagtt ttgcgggtgg ggg                33

<210> SEQ ID NO 20
<211> LENGTH: 18
<212> TYPE: DNA
<213> ORGANISM: Artificial Sequence
<220> FEATURE:
<223> OTHER INFORMATION: PCR Primer

<400> SEQUENCE: 20
cgcgcctaag cggccgcg                                 18

<210> SEQ ID NO 21
<211> LENGTH: 18
<212> TYPE: DNA
<213> ORGANISM: Artificial Sequence
<220> FEATURE:
<223> OTHER INFORMATION: PCR Primer

<400> SEQUENCE: 21
ggattcgccg gcgcagct                                 18

<210> SEQ ID NO 22
<211> LENGTH: 31
<212> TYPE: DNA
<213> ORGANISM: Artificial Sequence
<220> FEATURE:
<223> OTHER INFORMATION: PCR Primer

<400> SEQUENCE: 22
actgcgcgcc gtttgtttca tgacaaaagc c                  31

<210> SEQ ID NO 23
<211> LENGTH: 35
<212> TYPE: DNA
<213> ORGANISM: Artificial Sequence
<220> FEATURE:
<223> OTHER INFORMATION: PCR Primer

<400> SEQUENCE: 23
agtgcggccg cttactgctt tgatagagaa gcttg              35

<210> SEQ ID NO 24
<211> LENGTH: 27
<212> TYPE: DNA
<213> ORGANISM: Artificial Sequence
<220> FEATURE:
<223> OTHER INFORMATION: PCR Primer

<400> SEQUENCE: 24
gcacccagat acggttgcaa tcccgac                       27

<210> SEQ ID NO 25
<211> LENGTH: 32
<212> TYPE: DNA
<213> ORGANISM: Artificial Sequence
<220> FEATURE:
<223> OTHER INFORMATION: PCR Primer

<400> SEQUENCE: 25
gcatgcatct caattagtca gcaaccagga tc                 32

<210> SEQ ID NO 26
<211> LENGTH: 30

```
<212> TYPE: DNA
<213> ORGANISM: Artificial Sequence
<220> FEATURE:
<223> OTHER INFORMATION: PCR Primer

<400> SEQUENCE: 26
caattcagtt cgggtgatct ggtgttctcc                                    30

<210> SEQ ID NO 27
<211> LENGTH: 25
<212> TYPE: DNA
<213> ORGANISM: Artificial Sequence
<220> FEATURE:
<223> OTHER INFORMATION: PCR Primer

<400> SEQUENCE: 27
ttcgcagtcc agtgcttgag tttgg                                         25

<210> SEQ ID NO 28
<211> LENGTH: 21
<212> TYPE: DNA
<213> ORGANISM: Artificial Sequence
<220> FEATURE:
<223> OTHER INFORMATION: PCR Primer

<400> SEQUENCE: 28 gcccttcgg gctagaacgg g                                              21

<210> SEQ ID NO 29
<211> LENGTH: 27
<212> TYPE: DNA
<213> ORGANISM: Artificial Sequence
<220> FEATURE:
<223> OTHER INFORMATION: PCR Primer

<400> SEQUENCE: 29
ggtgcgtctt ggtagctcat tcccatg                                       27

<210> SEQ ID NO 30
<211> LENGTH: 26
<212> TYPE: DNA
<213> ORGANISM: Artificial Sequence
<220> FEATURE:
<223> OTHER INFORMATION: PCR Primer

<400> SEQUENCE: 30
cgaagacccc gatagagaca cgtttc                                        26

<210> SEQ ID NO 31
<211> LENGTH: 16
<212> TYPE: DNA
<213> ORGANISM: Artificial Sequence
<220> FEATURE:
<223> OTHER INFORMATION: RNA 1 fragment

<400> SEQUENCE: 31
cattcgcgcg cggtta                                                   16

<210> SEQ ID NO 32
<211> LENGTH: 16
<212> TYPE: DNA
<213> ORGANISM: Artificial Sequence
<220> FEATURE:
<223> OTHER INFORMATION: Mutated RNA 1 fragment

<400> SEQUENCE: 32
```

-continued

<210> SEQ ID NO 33
<211> LENGTH: 18
<212> TYPE: DNA
<213> ORGANISM: Artificial Sequence
<220> FEATURE:
<223> OTHER INFORMATION: ORF 6LA fragment

<400> SEQUENCE: 33
cgcgcctaag cggccgcg                                                   18

<210> SEQ ID NO 34
<211> LENGTH: 3107
<212> TYPE: DNA
<213> ORGANISM: flock house virus

<400> SEQUENCE: 34
gttttcgaaa caaataaaac agaaaagcga acctaaacaa tgactctaaa agttattctt      60
ggagaacacc agatcacccg aactgaattg ttagtcggga ttgcaaccgt atctgggtgc     120
ggtgccgtag tgtactgcat atccaagttc tggggctatg gggcaattgc gccctatcct     180
cagagtggag ggaaccgagt tacacgcgca ttgcaacggg ctgtcattga caaaacgaag     240
accccgatag agacacgttt ctatccgctt gacagcctgc gtaccgtgac gcctaagcgt     300
gtcgcagaca acgggcacgc cgtttcaggg gccgtacgtg atgccgcacg tcgtttgatc     360
gacgagtcca tcacggccgt tggaggatcc aaatttgagg tcaaccccaa cccaaactca     420
agcactggac tgcgaaacca tttccacttc gccgtcggtg atttggcaca agatttccgt     480
aatgacacac ctgcggatga tgccttcatc gtcggtgttg atgttgatta ttatgtcacc     540
gagcctgatg tgcttttaga gcacatgcgt ccagtagtgt tacacacctt aacccgaag     600
aaagtgagcg gttttgatgc tgactcacca ttcaccatta gaacaacttt ggttgaatat     660
aaggttagcg gtggagcagc atgggtccat ccagtttggg attggtgcga agctggtgag     720
tttatcgcta gcagagtccg taccagctgg aaggagtggt ttttacaact accactgcga     780
atgattggtt tggagaaggt tggctatcat aaaatccatc attgtagacc gtggactgat     840
tgtccagatc gtgcacttgt ctacactata ccgcaatatg tcatttggcg atttaattgg     900
attgataccg aactacacgt gcgaaaactg aaacggattg aataccagga cgaaaccaaa     960
cctggttgga acagattgga gtatgtgacc gacaagaatg aactgctggt ttccatcggt    1020
cgagaagggg agcatgctca gattactatc gagaaagaaa gttggatat gctctcggga    1080
ttatccgcca cccaatctgt caacgctagg cttatcggta tgggacacaa ggacccgcaa    1140
tacacatcca tgattgtcca gtattatact ggcaagaagg tagtgtcacc aattagtcca    1200
actgtgtata aacctacaat gccacgcgtc cattggccag taaccagtga cgcagatgta    1260
ccagaagtga gcgcgcgcca atacacactg cctatcgtga gtgactgtat gatgatgcca    1320
atgatcaagc gctgggaaac aatgtctgaa tcaattgaac gtagggtgac ttttgtcgcc    1380
aatgataaga aaccaagcga cagaatcgcc aaaatagccg aaacgtttgt taaattgatg    1440
aatgggccat tcaaagatct tgacccttg tcgattgaag aaacgattga acggctgaat    1500
aaaccgtccc aacaattaca acttagggcg ttttcgaaa tgattggagt taaacctcgt    1560
caattgattg agtcgttcaa caagaacgaa cctggaatga atctagccg gataatatcc    1620
ggttttccag acatacttt catcttgaaa gtttccagat acaccttagc gtattcggat    1680
atagttctac atgccgaaca caatgaacat tggtattacc ccgggcggaa cccgactgag    1740

```
atcgccgacg gtgtttgtga gtttgttagt gactgtgatg ctgaagtcat agaaactgac   1800
ttctccaacc tcgatggcag ggtttccagc tggatgcaaa gaaacatcgc ccaaaaggcc   1860
atggttcaag cattccgccc agaatacaga gatgagatca tttcattcat ggacacgata   1920
atcaattgtc cagctaaagc taaacgcttt ggtttccgat atgagcctgg tgtaggcgtt   1980
aaaagtggaa gtccaacaac cacgccacat aacacccaat acaatggatg tgtcgaattt   2040
acagctctga cctttgagca tcctgatgct gaacctgaag atttgttccg tttaatcgga   2100
ccgaagtgcg gtgatgatgg tctttcccgg gctatcattc aaaaatcaat taatcgcgct   2160
gccaagtgtt tcggcctcga actcaaagtt gaacgataca atccagagat aggtctttgt   2220
ttcctgtctc gtgtatttgt ggacccgctc gcaactacga ccacaattca agacccactg   2280
cgtactctgc gaaaactaca tcttacaaca agagatccaa cgataccatt agctgatgcg   2340
gcttgcgacc gtgtcgaagg ctatctctgt accgatgcgc ttactccgtt aatttcggat   2400
tattgcaaaa tggtactacg actctacggg cccactgctt caactgagca ggtgaggaac   2460
caacgtagaa gccggaataa agagaagccc tactggttga cttgtgacgg atcatggcca   2520
cagcatccgc aagacgccca tttgatgaag caggttttaa tcaaacgtac agccattgac   2580
gaagatcagg tcgatgcact cattgggcgt tttgccgcaa tgaaggatgt ctgggagaaa   2640
attacacatg acagcgagga gagcgccgct gcgtgtacgt ttgatgaaga cggcgttgcg   2700
ccgaactccg tggacgaatc gttaccaatg ttaaacgatg ccaagcaaac tcgcgctaat   2760
ccaggaactt cccgaccgca ttcaaacggc ggtggaagca gccatgggaa tgagctacca   2820
agacgcaccg aacaacgtgc gcagggacct cgacaacctg cacgcttgcc taaacaaggc   2880
aaaactaacg gtaagtcgga tggtaacatc actgctggag aaacccagcg tggtggcata   2940
cctagaggga aaggcccccg aggaggcaaa accaacactc gaagaacgcc tccgaaagct   3000
ggagctcagc cacagccttc caacaaccgg aagtgacccc ccacccgcaa aactgtaggt   3060
ggctcttagg agcacccaca cccgttctag cccgaaaggg cagaggt              3107
```

<210> SEQ ID NO 35
<211> LENGTH: 1031
<212> TYPE: PRT
<213> ORGANISM: flock house virus

<400> SEQUENCE: 35

```
Val Phe Glu Thr Asn Lys Thr Glu Lys Arg Thr Thr Met Thr Leu Lys
1               5                   10                  15

Val Ile Leu Gly Glu His Gln Ile Thr Arg Thr Glu Leu Leu Val Gly
            20                  25                  30

Ile Ala Thr Val Ser Gly Cys Gly Ala Val Val Tyr Cys Ile Ser Lys
        35                  40                  45

Phe Trp Gly Tyr Gly Ala Ile Ala Pro Tyr Pro Gln Ser Gly Gly Asn
    50                  55                  60

Arg Val Thr Arg Ala Leu Gln Arg Ala Val Ile Asp Lys Thr Lys Thr
65                  70                  75                  80

Pro Ile Glu Thr Arg Phe Tyr Pro Leu Asp Ser Leu Arg Thr Val Thr
                85                  90                  95

Pro Lys Arg Val Ala Asp Asn Gly His Ala Val Ser Gly Ala Val Arg
            100                 105                 110

Asp Ala Ala Arg Arg Leu Ile Asp Glu Ser Ile Thr Ala Val Gly Gly
        115                 120                 125
```

```
Ser Lys Phe Glu Val Asn Pro Asn Pro Asn Ser Ser Thr Gly Leu Arg
    130                 135                 140

Asn His Phe His Phe Ala Val Gly Asp Leu Ala Gln Asp Phe Arg Asn
145                 150                 155                 160

Asp Thr Pro Ala Asp Asp Ala Phe Ile Val Gly Val Asp Val Asp Tyr
                165                 170                 175

Tyr Val Thr Glu Pro Asp Val Leu Leu Glu His Met Arg Pro Val Val
            180                 185                 190

Leu His Thr Phe Asn Pro Lys Lys Val Ser Gly Phe Asp Ala Asp Ser
        195                 200                 205

Pro Phe Thr Ile Lys Asn Asn Leu Val Glu Tyr Lys Val Ser Gly Gly
    210                 215                 220

Ala Ala Trp Val His Pro Val Trp Asp Trp Cys Glu Ala Gly Glu Phe
225                 230                 235                 240

Ile Ala Ser Arg Val Arg Thr Ser Trp Lys Glu Trp Phe Leu Gln Leu
                245                 250                 255

Pro Leu Arg Met Ile Gly Leu Glu Lys Val Gly Tyr His Lys Ile His
            260                 265                 270

His Cys Arg Pro Trp Thr Asp Cys Pro Asp Arg Ala Leu Val Tyr Thr
        275                 280                 285

Ile Pro Gln Tyr Val Ile Trp Arg Phe Asn Trp Ile Asp Thr Glu Leu
    290                 295                 300

His Val Arg Lys Leu Lys Arg Ile Glu Tyr Gln Asp Glu Thr Lys Pro
305                 310                 315                 320

Gly Trp Asn Arg Leu Glu Tyr Val Thr Asp Lys Asn Glu Leu Leu Val
                325                 330                 335

Ser Ile Gly Arg Glu Gly Glu His Ala Gln Ile Thr Ile Glu Lys Glu
            340                 345                 350

Lys Leu Asp Met Leu Ser Gly Leu Ser Ala Thr Gln Ser Val Asn Ala
        355                 360                 365

Arg Leu Ile Gly Met Gly His Lys Asp Pro Gln Tyr Thr Ser Met Ile
    370                 375                 380

Val Gln Tyr Tyr Thr Gly Lys Lys Val Val Ser Pro Ile Ser Pro Thr
385                 390                 395                 400

Val Tyr Lys Pro Thr Met Pro Arg Val His Trp Pro Val Thr Ser Asp
                405                 410                 415

Ala Asp Val Pro Glu Val Ser Ala Arg Gln Tyr Thr Leu Pro Ile Val
            420                 425                 430

Ser Asp Cys Met Met Met Pro Met Ile Lys Arg Trp Glu Thr Met Ser
        435                 440                 445

Glu Ser Ile Glu Arg Arg Val Thr Phe Val Ala Asn Asp Lys Lys Pro
    450                 455                 460

Ser Asp Arg Ile Ala Lys Ile Ala Glu Thr Phe Val Lys Leu Met Asn
465                 470                 475                 480

Gly Pro Phe Lys Asp Leu Asp Pro Leu Ser Ile Glu Glu Thr Ile Glu
                485                 490                 495

Arg Leu Asn Lys Pro Ser Gln Gln Leu Gln Leu Arg Ala Val Phe Glu
            500                 505                 510

Met Ile Gly Val Lys Pro Arg Gln Leu Ile Glu Ser Phe Asn Lys Asn
        515                 520                 525

Glu Pro Gly Met Lys Ser Ser Arg Ile Ile Ser Gly Phe Pro Asp Ile
530                 535                 540

Leu Phe Ile Leu Lys Val Ser Arg Tyr Thr Leu Ala Tyr Ser Asp Ile
```

-continued

```
            545                 550                 555                 560
        Val Leu His Ala Glu His Asn Glu His Trp Tyr Tyr Pro Gly Arg Asn
                        565                 570                 575
        Pro Thr Glu Ile Ala Asp Gly Val Cys Glu Phe Val Ser Asp Cys Asp
                        580                 585                 590
        Ala Glu Val Ile Glu Thr Asp Phe Ser Asn Leu Asp Gly Arg Val Ser
                        595                 600                 605
        Ser Trp Met Gln Arg Asn Ile Ala Gln Lys Ala Met Val Gln Ala Phe
                        610                 615                 620
        Arg Pro Glu Tyr Arg Asp Glu Ile Ile Ser Phe Met Asp Thr Ile Ile
        625                 630                 635                 640
        Asn Cys Pro Ala Lys Ala Lys Arg Phe Gly Phe Arg Tyr Glu Pro Gly
                        645                 650                 655
        Val Gly Val Lys Ser Gly Ser Pro Thr Thr Thr Pro His Asn Thr Gln
                        660                 665                 670
        Tyr Asn Gly Cys Val Glu Phe Thr Ala Leu Thr Phe Glu His Pro Asp
                        675                 680                 685
        Ala Glu Pro Glu Asp Leu Phe Arg Leu Ile Gly Pro Lys Cys Gly Asp
                        690                 695                 700
        Asp Gly Leu Ser Arg Ala Ile Ile Gln Lys Ser Ile Asn Arg Ala Ala
        705                 710                 715                 720
        Lys Cys Phe Gly Leu Glu Leu Lys Val Glu Arg Tyr Asn Pro Glu Ile
                        725                 730                 735
        Gly Leu Cys Phe Leu Ser Arg Val Phe Val Asp Pro Leu Ala Thr Thr
                        740                 745                 750
        Thr Thr Ile Gln Asp Pro Leu Arg Thr Leu Arg Lys Leu His Leu Thr
                        755                 760                 765
        Thr Arg Asp Pro Thr Ile Pro Leu Ala Asp Ala Ala Cys Asp Arg Val
        770                 775                 780
        Glu Gly Tyr Leu Cys Thr Asp Ala Leu Thr Pro Leu Ile Ser Asp Tyr
        785                 790                 795                 800
        Cys Lys Met Val Leu Arg Leu Tyr Gly Pro Thr Ala Ser Thr Glu Gln
                        805                 810                 815
        Val Arg Asn Gln Arg Arg Ser Arg Asn Lys Glu Lys Pro Tyr Trp Leu
                        820                 825                 830
        Thr Cys Asp Gly Ser Trp Pro Gln His Pro Gln Asp Ala His Leu Met
                        835                 840                 845
        Lys Gln Val Leu Ile Lys Arg Thr Ala Ile Asp Glu Asp Gln Val Asp
                        850                 855                 860
        Ala Leu Ile Gly Arg Phe Ala Ala Met Lys Asp Val Trp Glu Lys Ile
        865                 870                 875                 880
        Thr His Asp Ser Glu Glu Ser Ala Ala Ala Cys Thr Phe Asp Glu Asp
                        885                 890                 895
        Gly Val Ala Pro Asn Ser Val Asp Glu Ser Leu Pro Met Leu Asn Asp
                        900                 905                 910
        Ala Lys Gln Thr Arg Ala Asn Pro Gly Thr Ser Arg Pro His Ser Asn
                        915                 920                 925
        Gly Gly Gly Ser Ser His Gly Asn Glu Leu Pro Arg Arg Thr Glu Gln
                        930                 935                 940
        Arg Ala Gln Gly Pro Arg Gln Pro Ala Arg Leu Pro Lys Gln Gly Lys
        945                 950                 955                 960
        Thr Asn Gly Lys Ser Asp Gly Asn Ile Thr Ala Gly Glu Thr Gln Arg
                        965                 970                 975
```

Gly Gly Ile Pro Arg Gly Lys Gly Pro Arg Gly Gly Lys Thr Asn Thr
            980                 985                 990

Arg Arg Thr Pro Pro Lys Ala Gly  Ala Gln Pro Gln Pro  Ser Asn Asn
        995                 1000                1005

Arg Lys  Pro Pro Thr Arg Lys  Thr Val Gly Gly Ser  Glu His Pro
    1010                1015                1020

His Pro  Phe Pro Glu Arg Ala  Glu
    1025                1030

<210> SEQ ID NO 36
<211> LENGTH: 986
<212> TYPE: PRT
<213> ORGANISM: flock house virus

<400> SEQUENCE: 36

Phe Ser Lys Gln Ile Lys Gln Lys Ser Glu Pro Lys Gln Leu Lys Leu
1               5                   10                  15

Phe Leu Glu Asn Thr Arg Ser Pro Glu Leu Asn Cys Ser Gly Leu Gln
            20                  25                  30

Pro Tyr Leu Gly Ala Val Pro Cys Thr Ala Tyr Pro Ser Ser Gly Ala
        35                  40                  45

Met Gly Gln Leu Arg Pro Ile Leu Arg Val Glu Gly Thr Glu Leu His
    50                  55                  60

Ala His Cys Asn Gly Leu Ser Leu Thr Lys Arg Arg Pro Arg Arg His
65                  70                  75                  80

Val Ser Ile Arg Leu Thr Ala Cys Val Pro Arg Leu Ser Val Ser Gln
                85                  90                  95

Thr Thr Gly Thr Pro Phe Gln Gly Pro Tyr Val Met Pro His Val Val
            100                 105                 110

Ser Thr Ser Pro Ser Arg Pro Leu Glu Asp Pro Asn Leu Arg Ser Thr
        115                 120                 125

Pro Thr Gln Thr Gln Ala Leu Asp Cys Glu Thr Ile Ser Thr Ser Pro
    130                 135                 140

Ser Val Ile Trp His Lys Ile Ser Val Met Thr His Leu Arg Met Met
145                 150                 155                 160

Pro Ser Ser Ser Val Leu Met Leu Ile Ile Met Ser Pro Ser Leu Met
                165                 170                 175

Cys Phe Ser Thr Cys Val Gln Cys Tyr Thr Pro Leu Thr Arg Arg Lys
            180                 185                 190

Ala Val Leu Met Leu Thr His His Ser Pro Leu Arg Thr Thr Trp Leu
        195                 200                 205

Asn Ile Arg Leu Ala Val Glu Gln His Gly Ser Ile Gln Phe Gly Ile
    210                 215                 220

Gly Ala Lys Leu Val Ser Leu Ser Leu Ala Glu Ser Val Pro Ala Gly
225                 230                 235                 240

Arg Ser Gly Phe Tyr Asn Tyr His Cys Glu Leu Val Trp Arg Arg Leu
                245                 250                 255

Ala Ile Ile Lys Ser Ile Ile Val Asp Arg Gly Leu Ile Val Gln Ile
            260                 265                 270

Val His Leu Ser Thr Leu Tyr Arg Asn Met Ser Phe Gly Asp Leu Ile
        275                 280                 285

Gly Leu Ile Pro Asn Tyr Thr Cys Glu Asn Asn Gly Leu Asn Thr Arg
    290                 295                 300

Thr Lys Pro Asn Leu Val Gly Thr Asp Trp Ser Met Pro Thr Arg Met

```
                305                 310                 315                 320
Asn Cys Trp Phe Pro Ser Val Glu Lys Gly Ser Met Leu Arg Leu Leu
                325                 330                 335
Ser Arg Lys Lys Ser Trp Ile Cys Ser Arg Asp Tyr Pro Pro Asn
        340                 345                 350
Leu Ser Thr Leu Gly Leu Ser Val Trp Asp Thr Arg Thr Arg Asn Thr
            355                 360                 365
His Pro Leu Ser Ser Ile Ile Leu Ala Arg Arg Cys His Gln Leu Val
        370                 375                 380
Gln Leu Cys Ile Asn Leu Gln Cys His Ala Ser Ile Gly Gln Pro Val
385                 390                 395                 400
Thr Gln Met Tyr Gln Lys Ala Arg Ala Asn Thr His Cys Leu Ser Val
            405                 410                 415
Thr Val Cys Gln Ser Ser Ala Gly Lys Gln Cys Leu Asn Gln Leu Asn
            420                 425                 430
Val Gly Leu Leu Ser Pro Met Ile Arg Asn Gln Ala Thr Glu Ser Pro
            435                 440                 445
Lys Pro Lys Arg Leu Leu Asn Met Gly His Ser Lys Ile Leu Thr Leu
        450                 455                 460
Cys Arg Leu Lys Lys Arg Leu Asn Gly Ile Asn Arg Pro Asn Asn Tyr
465                 470                 475                 480
Asn Leu Gly Arg Phe Ser Lys Leu Glu Leu Asn Leu Val Asn Leu Ser
                485                 490                 495
Arg Ser Thr Arg Thr Asn Leu Glu Asn Leu Ala Gly Tyr Pro Val Phe
            500                 505                 510
Gln Thr Tyr Phe Ser Ser Lys Phe Pro Asp Thr Pro Arg Ile Arg Ile
        515                 520                 525
Phe Tyr Met Pro Asn Thr Met Asn Ile Gly Ile Thr Pro Gly Gly Thr
        530                 535                 540
Arg Leu Arg Ser Pro Thr Val Phe Val Ser Leu Leu Val Thr Val Met
545                 550                 555                 560
Leu Lys Ser Lys Leu Thr Ser Pro Thr Ser Met Ala Gly Phe Pro Ala
                565                 570                 575
Gly Cys Lys Glu Thr Ser Pro Lys Arg Pro Trp Phe Lys His Ser Ala
            580                 585                 590
Gln Asn Thr Glu Met Arg Ser Phe His Ser Trp Thr Arg Ser Ile Val
        595                 600                 605
Gln Leu Lys Leu Asn Ala Leu Val Ser Asp Met Ser Leu Val Ala Leu
        610                 615                 620
Lys Val Glu Val Gln Gln Pro Arg His Ile Thr Pro Asn Thr Met Asp
625                 630                 635                 640
Val Ser Asn Leu Gln Leu Pro Leu Ser Ile Leu Met Leu Asn Leu Lys
            645                 650                 655
Ile Cys Ser Val Ser Asp Arg Ser Ala Val Met Met Val Phe Pro Gly
            660                 665                 670
Leu Ser Phe Lys Asn Gln Leu Ile Ala Leu Pro Ser Val Ser Ala Ser
            675                 680                 685
Asn Ser Lys Leu Asn Asp Thr Ile Gln Arg Val Phe Val Ser Cys Leu
        690                 695                 700
Val Tyr Leu Trp Thr Arg Ser Gln Leu Arg Pro Gln Phe Lys Thr His
705                 710                 715                 720
Cys Val Leu Cys Glu Asn Tyr Ile Leu Gln Gln Glu Ile Gln Arg Tyr
            725                 730                 735
```

-continued

```
His Leu Met Arg Leu Ala Thr Val Ser Lys Ala Ile Ser Val Pro Met
            740                 745                 750

Arg Leu Leu Arg Phe Arg Ile Ile Ala Lys Trp Tyr Tyr Asp Ser Thr
            755                 760                 765

Gly Pro Leu Leu Gln Leu Ser Arg Gly Thr Asn Val Glu Ala Gly Ile
    770                 775                 780

Lys Arg Ser Pro Thr Gly Leu Val Thr Asp His Gly His Ser Ile Arg
785                 790                 795                 800

Lys Thr Pro Ile Ser Arg Phe Ser Asn Val Gln Pro Leu Thr Lys Ile
                805                 810                 815

Arg Ser Met His Ser Leu Gly Val Leu Pro Gln Arg Met Ser Gly Arg
            820                 825                 830

Lys Leu His Met Thr Ala Arg Arg Ala Pro Leu Arg Val Arg Leu Met
            835                 840                 845

Lys Thr Ala Leu Arg Arg Thr Pro Trp Thr Asn Arg Tyr Gln Cys Thr
850                 855                 860

Met Pro Ser Lys Leu Ala Leu Ile Gln Glu Leu Pro Asp Arg Ile Gln
865                 870                 875                 880

Thr Ala Val Glu Ala Ala Met Gly Met Ser Tyr Gln Asp Ala Pro Asn
                885                 890                 895

Asn Val Arg Arg Asp Leu Asp Asn Leu His Ala Cys Leu Asn Lys Ala
            900                 905                 910

Lys Leu Thr Val Ser Arg Met Val Thr Ser Leu Leu Glu Lys Pro Ser
            915                 920                 925

Val Val Ala Tyr Leu Glu Gly Lys Ala Pro Glu Glu Ala Lys Pro Thr
    930                 935                 940

Leu Glu Glu Arg Leu Arg Lys Leu Glu Leu Ser His Ser Leu Pro Thr
945                 950                 955                 960

Thr Gly Ser Asp Pro Pro Ala Lys Leu Val Ala Leu Arg Ser Thr
                965                 970                 975

His Thr Arg Ser Ser Pro Lys Gly Gln Arg
            980                 985
```

MODIFIED NODAVIRUS RNA FOR GENE DELIVERY

TECHNICAL FIELD

This invention is in the field of gene delivery, more particularly in the delivery of genes for expression using modified nodavirus RNA packaged in virus-like particles (VLPs).

BACKGROUND ART

The Nodaviridae have bipartite RNA genomes, that is to say their genomes consist of two separate single-stranded RNA molecules, designated RNA1 and RNA2. These are both packaged within the same virion. RNA1 encodes an RNA replicase, and RNA2 encodes the virion capsid protein. In flock house virus (FHV), RNA1 is 3.1 kb long and RNA2 is 1.4 kb.

The replicase product of FHV RNA1 is specific for the viral genome and this enables FHV to replicate autonomously [Ball et al. (1992) J. Virol. 66:2326–34: Gallagher et al. (1983) J. Virol. 46:481–89]. In a natural situation, the replicase is highly template specific and replicates only viral RNA1 and RNA2, but self-replication also occurs in the absence of RNA2. Furthermore, even though FHV is an insect virus, it can self-replicate in many different cell types, including plants, vertebrates and yeasts.

Manipulation of RNA2 and the FHV capsid protein has been widely reported. The insertion of HIV epitopes into surface loops has been reported [e.g. Scodeller et al. (1995) Vaccine 13:1233–39; Buratti et al. (1996) J. Immunol. Methods 197:7–18; Schiappacassi et al. (1997) J. Virol. Methods 63:121–27]. More generally, the virion has been used as an epitope display system [Lorenzi & Burrone (1999) Immunotechnol. 4:267–72; see also WO96/05293].

In contrast, manipulation of FHV RNA1 and the replicase has not been pursued. In fact, the self-replication function of RNA1 has been shown to be very sensitive to manipulation of RNA1 and its ORF [Ball (1995) J. Virol 69:720–727].

During replication of RNA1, a small sub-genomic RNA called RNA3 is also transcribed from the 3' end of RNA1, RNA3 encodes for two small proteins of unknown function: B1 (in the same open reading frame and with the same translational stop codon as the replicase) and B2 (in the +1 open reading frame with respect to the replicase) [Ball (1992) J. Virol 66:2335–45; Johnson & Ball (1999) J. Virol. 73:7933–79421. Transcription of RNA3 seems to be controlled by an internal promoter which becomes active when a double stranded RNA+/RNA− intermediate is formed. It is an object of invention to permit modification and manipulation of the RNA1 molecule to exploit its ability to self-replicate, and to provide such modified RNA1 molecules.

DISCLOSURE OF THE INVENTION

The invention provides a modified nodavirus RNA1 molecule which includes a heterologous insertion downstream of the replicase ORFs of said RNA1. The insertion is preferably downstream of the replicase and B2 ORFs of said RNA 1.

The RNA1 Molecule

The invention is based around the RNA1 molecule of a nodavirus. RNA1 encodes an RNA replicase which specifically replicates the nodavirus genome, and sequences from several nodaviruses are available e.g. flock house virus (accession X77156), black beetle virus (accession X02396 & K02560), striped jack nervous necrosis virus (AB025018), pariacoto virus (AF171942), nodamura virus (AF174533), black beetle virus (NC_001411), and halibut nervous necrosis virus (AJ401165).

In relation to the present invention, a 'nodavirus RNA1' sequence includes a sequence found in nature, as well as fragments, variants and mutants thereof that encode replicases which retain the ability to specifically amplify their own genes.

It will be appreciated that the RNA1 molecule of the invention may be prepared by modification of a RNA1 obtained from a nodavirus by using standard molecular biology techniques, or may be assembled synthetically by enzymatic and/or chemical means.

ORFs Within the RNA1 Molecule

The available RNA1 sequences for nodaviruses (see above) indicate the location of the replicase (or 'A') and 'B2' ORFs. The insertion in the molecules of the present invention is downstream of the replicase ORF, and preferably also downstream of the B2 ORF.

In FHV, RNA1 is 3107 nucleotides long. The replicase ORF is encoded by nucleotides 40-3033, and the B2 ORF is encoded by nucleotides 2738-3055. According to the invention, therefore, the heterologous insertion for FHV is situated between nucleotides 3033 and 3107, and preferably between nucleotides 3055 and 3107.

Preferably, the heterologous insertion is more than 5 nucleotides downstream of the replicase ORF (i.e. downstream of nucleotide 3038 in FHV) e.g. more than 10, 15, 20, 25, 30, 35, 40, 45 or 50 nt downstream. More preferably, it is more than 5 nucleotides downstream of the B2 ORF (i.e. downstream of nucleotide 3060 in FHV) e.g. more than 10, 15, 20, 25, 30, 35, 40, 45 or 50 nt downstream of the ORFs. Similarly, the heterologous insertion is preferably more than 5 nucleotides upstream of 3' end of RNA1 (i.e. upstream of nucleotide 3102 in FHV) e.g. more than 10, 15, 20, 25, 30, 35, 40, 45 or 50 nt upstream of the 3' end. Retaining a length of native 3' terminal sequence of a RNA1 helps ensure that the RNA1 retains its ability to self-replicate (Ball (1995) *J. Virol* 69:720–72].

If the heterologous insertion is within 3 nucleotides of the final codon in the replicase or B2 ORF (i.e. between nucleotides 3034–3036 or 3056–3058), it is preferred that the 5' end of the insertion maintains a stop codon for the ORF (i.e. a stop codon at nucleotides 3034–3036 for the replicase or at 3056–3058 for B2).

The Heterologous Insertion

The modified RNA1 of the invention carries a heterologous insertion. This insertion preferably comprises one or more protein-coding regions, with their own start and stop codons.

As the insertion is downstream of one or more ORFs native to RNA1, to assist in its translation the 5' portion of the heterologous insertion may also comprise a sequence that directs cap-independent translation. Typically, therefore, the heterologous insertion will comprise an internal ribosome entry site (IRES) functionally linked to a protein coding region. Any suitable IRES can be used, such as the hepatitis C virus or encephalomyocarditis virus IRES, or those from picornaviruses, foot-and-mouth disease, virus, echovirus 11', classical swine fever virus, the c-myc proto-oncogene etc. [e.g. Martinez-Salas (1999) *Curr. Opin. Biotechnol.* 10:458–464].

The heterologous insertion does not destroy the ability of the RNA1 to self-replicate via its encoded replicase. Thus the modified RNA1 can deliver a gene of interest for expression, and is able to direct its own replication.

Packaging the Modified RNA1

In order to deliver the modified RNA1 to a cell, it is preferred to package it e.g. within a virus-like particle (VLP) or pseudovirion.

A nodavirus particle may be used, comprising protein expressed from RNA2 (optionally modified). If this approach is used, the RNA2 is preferably from the same nodavirus as the modified RNA1 which is packaged.

As nodaviruses are native to insect cells, however, where delivery to a mammalian cell is desired, it is preferred to use a different package. A preferred package is a papillomavirus VLP [e.g. Touze & Coursaget (1998) *Nucl. Acid. Res.* 26:1317–1323; Kawana et al. (1998) *J. Virol.* 72:10298–10300; Müller et al. (1997) *Virol.* 234:93–111; Zhao et al. (1998) *Virol.* 243:482–491; Unckell et al. (1997) *J. Virol.* 71:2934–2939; WO97/46693; WO98/02548 etc.], which is able to bind to receptors on mammalian cells.

Using HPV VLPs offers several advantages. Firstly, HPV VLPs bind to a wide range of cell types, with the highest level of binding being observed with epithelial and mesenchymal cells, and only low levels of anti-VLP antibodies have been observed in humans [Le Cann et al. (1995) *J Clin. Microbiol.* 33:1380–1382]. Secondly, L1 proteins of different HPV type can be expressed so, as immunity induced by the use of VLPs is predominantly type specific, the presence of pre-existing anti-HPV antibodies may be eluded and multiple immunisations may be feasible. Thirdly, as nodavirus RNA1 is small, it can overcome a known limitation with HPV VLPs, namely the upper limit of 7–8 kbp on encapsidated nucleic acid. Nodavirus RNA thus offers significant advantages over other nucleic acid.

The papillomavirus is preferably a human papillomavirus, such as HPV-6. The VLP capsid may comprise proteins L1 and L2, or may be made solely of L1.

In order to facilitate packaging of the modified RNA 1, the proteins which form the package (e.g. the capsid proteins in a VLP) may be modified to include a sequence or structure which can interact specifically with the modified RNA1. The in vivo specificity of RNA/protein interactions is a further advantage of using nodavirus RNA, compared with problems encountered using DNA plasmids.

A particularly useful packaging system of this type relies on the tat/TAR interaction of immunodeficiency viruses (e.g. HIV, BIV, etc.). In this system, the package includes a motif from the tat protein (e.g. a minimal tat sequence, such as amino acids 48–59 of HIV tat: see also Derse et al. (1991) *J. Virol* 65:7012–15; Chen & Frankel (1994) *Biochemistry* 33: 2708–2715: Puglisi et al. (1995) *Science* 270: 1200–1202) that specifically interacts with a TAR motif (e.g. a minimal TAR sequence, such as the minimal 59 mer, or the motifs described in WO92/02228) in the modified RNA1, Thus the modified RNA1 of the invention will additionally comprise a TAR motif. This may be upstream or downstream of a gene within the heterologous insertion, but is preferably downstream. As an alternative, the TAR motif may be placed upstream of the replicase ORF (i.e. before nucleotide 40 in FHV). In a papillomavirus-based packaging system, a tat sequence may be inserted in the L1 protein, preferably at or near the C-terminal. Although this region is not essential for capsid formation [Paintsil et al (1996) Virology 223:238–244], the sequence must not disrupt the ability of the VLP to assemble [Müller et al. (1997) *Virology* 234:93–111]. The tat and TAR interaction results in packaging of the modified RNA1 within the package. Use of the tat/TAR interaction from BIV is preferred, as this is a strong interaction that requires no cellular factors.

It will be appreciated that the use of the tat/TAR interaction for packaging nucleic acids within a VLP is not restricted to the modified RNA1 of the invention.

Further Aspects of the Invention

The modified RNA1 of the invention is typically positive-sense and single-stranded. The invention also provides: (i) single-stranded nucleic acid complementary to RNA1 of the invention. (ii) single-stranded nucleic acid complementary to ti): (iii) single-stranded nucleic acid comprising a sequence complementary to RNA1 of the invention: (iv) single-stranded nucleic acid comprising a sequence complementary to (i): and (v) double-stranded nucleic acid in which one of the strands is (i), (ii), (iii) or (iv). The term 'nucleic acid' encompasses RNA, DNA, as well as analogs such as PNA (peptide nucleic acid) and backbone-modified DNA or RNA (e.g. phosphorothioates etc.). It will be appreciated that nucleic acid can be transcribed by RNA polymerase in vitro or in vivo to produce the modified RNA1 of the invention.

The invention also provides a VLP containing nucleic acid of the invention (e.g. containing a modified RNA1). The VLP is preferably a papillomavirus VLP.

The invention also provides a papillomavirus L1 protein modified to include a motif from an immunodeficiency virus tat protein.

The invention also provides a process for producing a modified RNA1 molecule of the invention, comprising the steps of: (a) obtaining nucleic acid comprising or encoding a nodavirus RNA1 sequence: and (b) inserting a heterologous sequence downstream of the replicase ORF and B2 ORF within said RNA1 sequence. Where FHV is used, it should be noted that its replicase shows maximal activity below 28° C.

The invention also provides a process for producing a VLP of the invention, comprising the steps of: transfecting a cell with nucleic acid according to the invention: transfecting a cell with nucleic acid encoding a VLP capsid protein, optionally modified to include a motif specific for modified RNA1: and purifying VLPs from the cell. This process preferably takes place in yeast.

In order to introduce VLP-encoding and RNA1-encoding nucleic acid into the same yeast, it is possible to mate haploid strains (e.g. a haploid strain expressing a capsid protein can be mated with a haploid strain of opposite mating type expressing RNA1).

Nucleic acid (especially modified RNA1) and VLPs of the invention are also provided for use as medicaments. They are particularly useful for gene delivery eg. in gene therapy.

The invention also provides a process for delivering a nucleic acid sequence to a cell, comprising the step of introducing a VLP of the invention into said cell. This process may be carried out in vitro (cells in culture) or in vivo.

Nodaviruses

Nodaviruses are divided into the alphanodaviruses and the betanodaviruses, and include Nodamura virus, black beetle virus, Boolarra virus, flock house virus (FHV). gypsy moth virus. Manawatu virus, atlantic halibut virus, tiger puffer nervous necrosis virus. barfin flounder nervous necrosis virus, Japanese flounder nervous necrosis virus. Dicentrarchus labrax encephalitis virus, pariacoto virus, dragon nervous necrosis virus, halibut nervous necrosis virus, malabaricus nervous necrosis virus, redspotted grouper nervous necrosis virus, umbrina cirrosa nodavirus, and striped Jack nervous necrosis virus. RNA1 molecules from any of these viruses may be used according to the invention. As the best-studied nodaviruses at the molecular level, however, FHV and Nodamura virus are preferred. Further details of nodaviruses can be found in Garzon & Charpentier [pages 351–370 of *Atlas of invertebrate viruses* (eds. Adams & Bonami). CRC press (1992)] and in Hendry [pages 227–276 of *Viruses of invertebrates* (ed. Kurstak), Marcel Deker (1991)].

BRIEF DESCRIPTION OF DRAWINGS

FIG. 1 shows cDNA from FHV RNA1 (SEQ ID NO: 34). The start codons for the replicase (40), B1 (2728) and B2 (2738) are boxed. The reading frames for (a) replicase/B1 (SEQ ID NO: 35) and (b) B2 (SEQ ID NO: 36) are both shown for the complete genome. The start of the RapApep fragment expressed in *E. coli* is underlined.

FIG. 2 is a schematic representation of the pFHV[1.0] plasmid. The HDV ribozyme is hatched, and the transcription terminator is black.

FIG. 3 shows restriction sites with the RNA1 region of pFHV[1.0]

FIG. 4 shows the removal of a BssHII site in RNA1. The original sequence and the mutated sequence are shown as SEQ ID NO: 31 and 32, respectively.

FIGS. 6 Parts A–C and 7 Parts A–F show the construction of pFHV-MutΔ and pSK$^+$-ADH$_2$-RNA1/SpeI, respectively.

FIG. 21 Parts A–B shows constructs for His-tagged *E. coli* expression of replicase and B2, and FIG. 22 Parts A–B shows SDS-PAGE of proteins expressed from these constructs. Lane 1 of 22(A) is a MW market plus fraction 14; lanes 2 to 9 are fractions 15 to 22: lane 10 is column flow-through. Lane 1 of 22(B) is the soluble fraction of cellular lysis: lane 2 is column flow-through: lanes 3 to 11 are fractions 21 to 29: lane 12 is a MW marker.

MODES FOR CARRYING OUT THE INVENTION

The RNA1 of FHV

The sequence of RNA1 from the FHV genome is given in GenBank as accession number X77156. A double-stranded cDNA (3107 bp) corresponding to the RNA1 is shown in FIG. 1 (SEQ ID NO: 34).

This cDNA is present in plasmid pFHV[1,0], described by Ball [*J. Virol.* (1995) 69:720–727], which was used in subsequent experiments. pFHV[1,0] also includes: an 18 bp T7 promoter upstream from the RNA1 sequence, with a single G between the promoter and the RNA1 5' end; a hepatitis delta virus ribozyme (89 bp) positioned downstream of the RNA1 sequence, such that cleavage of the ribozyme generates the native 3' end of RNA1; and a 136 bp T7 transcriptional terminator which seems to assist ribozyme activity. This is shown in FIG. 2.

Modification of RNA1 for Cloning Purposes

To facilitate cloning, various changes were made to RNA1.

Removal of a BssHII Site.

As shown in FIG. 3, the native RNA1 sequence includes two nearby BssHII restriction sites (nucleotides 1270 and 1278). One of these was removed by introducing a silent mutation that did not affect the replicase amino acid sequence.

Figure 5:
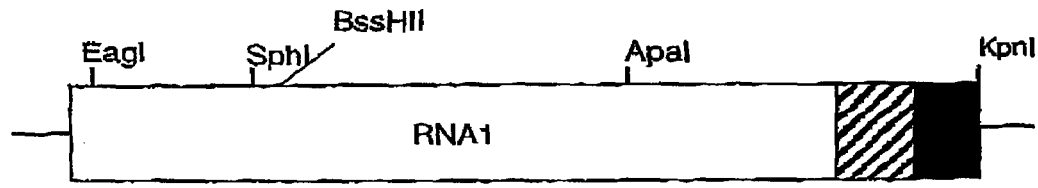
FIG. 5 shows pFHV-BsshIIΔ.

The SphI/BsshII fragment of RNA1 was replaced by a PCR fragment generated using primers RI900-f and RI1272M-r (Table I). The first primer included the SphI site necessary for cloning, while the sequence of the reverse primer included a G to A mutation at position 1271, thereby eliminating one of the two BsshII restriction sites (FIG. 4) without altering the replicase ORF. The resulting plasmid was called pFHV-BsshIIΔ (FIG. 5).

Introduction of Additional Sites.

In order to insert heterologous sequences into RNA1, two additional restriction sites were introduced: a SacII site at position 3062, a NotI site at position 3072 (downstream from the translational stop codons for the replicase and B2 ORFs). In addition, a Unique SalI site was inserted into pFHV[0,1] downstream from the T7 transcriptional terminator (nucleotide 3337). These sites were introduced by PCR amplification, as follows (FIG. 6):

primers ApaI-f and DRS-r (Table I) amplified a fragment of RNA1 between the ApaI site (position 2349) and position 3101. Introduction of the SacII and NotI restriction sites was achieved by introducing the two sequences in the DRS-r primer (FIG. 6a).

primers DRS-f (complementary to DRS-r) and RI-KpnI-r amplified a fragment spanning the region from nucleotide 3039 to the KpnI site (position 3368) (FIG. 6a).

The fusion of the two DNA fragments was obtained by denaturing and mixing equal amounts of the two amplification products which annealed by means of a 62 bp complementary region present in the two PCR fragments. Following elongation cycles with Taq polymerase in the only presence of dNTPs and amplification cycles in the presence of Taq and primers ApaI-f and RI-KpnI-r, a blunt ended DNA fusion fragment was obtained (FIG. 6b) which was then cloned in pCR2.1 vector to check the DNA sequence. The ApaI-KpnI fragment was excised from pCR2.1 and used to replace the homologous fragment in pFHV[1,0] and pFHV-BsshIIΔ, obtaining a plasmid named pFHV-Mut (not shown) and a plasmid named pFHV-MutΔ (FIG. 6c), containing the entire RNA1 cDNA with only one BsshII site and the new SacII, NotI and SalI restriction sites.

Cloning of RNA1 into Yeast Vector

In order to express RNA1 (and modified versions of it) in yeast, the cDNA was cloned into a yeast vector, downstream of a yeast-specific promoter. This vector directs the transcription of RNA1 molecules that encode the replicase and (after ribozyme cleavage) have 5' and 3' ends compatible with self-replication. The overall approach is shown in FIG. 7.

Cloning of $ADH_2$/GAP in pBluescript SK+.

Figure 8:
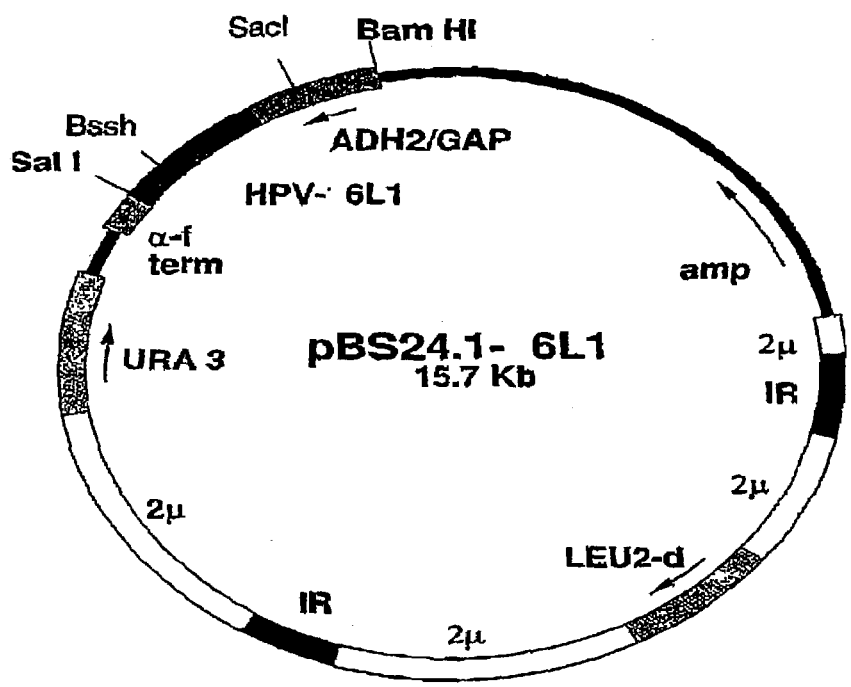
FIG. 8 shows pBS24.1-6L1.

The promoter used for expression was the $ADH_2$/GAP promoter. As a source of this promoter, yeast expression vector pBS24.1-6L1 (FIG. 8; see also WO00/09699) was used. The DNA fragment $ADH_2$/GAP-6L1 was extracted from plasmid PBS24.1-6L1 by digestion with SacI and SalI, and was cloned in pBluescript-SK+ (Stratagene) digested with the same enzymes. The resulting construct was named pSK+-ADH-6L1.

PCR amplification of the Yeast $ADH_2$/GAP Promoter.

A portion of the yeast promoter was amplified by PCR carried out on pSK+-ADH-6L1 using primer ADH/Sac (Table I), which anneals on the yeast promoter at the SacI site, and reverse primer P-R1rev, which anneals on the promoter at the fusion with the 6L1 gene, which additionally included 13 nucleotides from RNA1 (FIG. 7a).

PCR Amplification of RNA1/Sph.

A portion of RNA1 cDNA from pFHV[1,0] was amplified using primer RNA1-f, which anneals at the 5' end of RNA1 (+1 position), and reverse primer RNA1-r, which anneals at the unique SphI restriction site at nucleotide 1021 (FIG. 7b).

ADH2-RNA1/Sph fusion.

The fusion was obtained by denaturing and mixing equal amounts of the two amplification products of FIGS. 7a & b, thus favouring the annealing of the 13 bp complementary region present in both PCR fragments (FIG. 7c). Following elongation cycles with Taq only in the presence of dNTPs and amplification cycles in the presence of Taq and the primers ADH/SAC and RNA1-r, a fusion blunt ended DNA fragment was obtained.

Cloning of the ADH2-RNA1/Sph in pCR2.1.

This blunt ended PCR product was cloned in pCR2.1 (Invitrogen), giving plasmid pCR-ADH2/RNA1 (FIG. 7d). Its DNA sequence was checked, and confirmed the expected promoter/RNA1 fusion sequence TAAATCTA GTTTC-GAAA, although some mutations were present in other regions of the amplified product. The only clone which had a correct amplified sequence, however, had a mutation which eliminated the SphI site necessary for the further steps (FIG. 7d).

Cloning of the ADH/RNA1 Fusion Product in pSK+-ADH2-6L1.

To overcome this problem, the fusion product was excised from pCR2.1 as a SacI-Spe fragment and cloned into pSK+-ADH2-6L1 (FIG. 7e) digested with the same restriction enzymes, thus obtaining the final construct pSK+-ADH2-RNA1/SpeI (FIG. 7f).

Introducing Modified RNA1 into the Yeast Vector.

Figure 9:
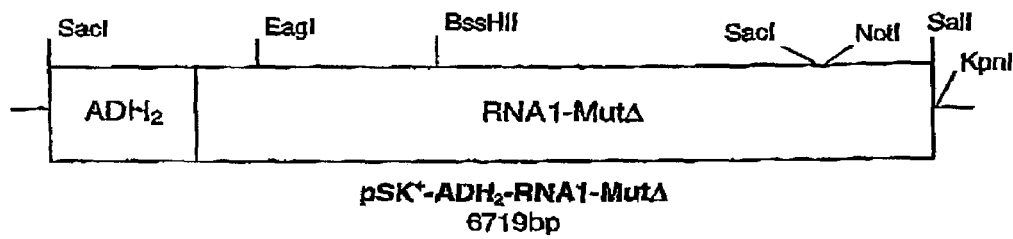
FIG. 9 shows pSL$^+$-ADH$_2$-RNA1-MutΔ.

The EagI-KpnI fragment from pFHV-BsshIIΔ (FIG. 5) was inserted in place of the corresponding fragment in pSK+-ADH2-RNA1/SpeI (FIG. 7f), generating a construct named pSK+-ADH2-RNA1-BsshIIΔ. The BsshII-KpnI fragment in this construct was replaced with the corresponding fragment from pFHV-MutΔ (FIG. 6c), generating a plasmid named pSK+-ADH2-RNA1-MutΔ (FIG. 9).

Insertion of Heterologous Sequences

A heterologous insertion was made inside the RNA1 sequence. A gene for expressing green fluorescent protein (GFP) [Chalfie et al. (1994) *Science* 263:802–806] was inserted downstream from the replicase and B2 open reading frames, together with a TAR sequence from HIV.

Figure 10:
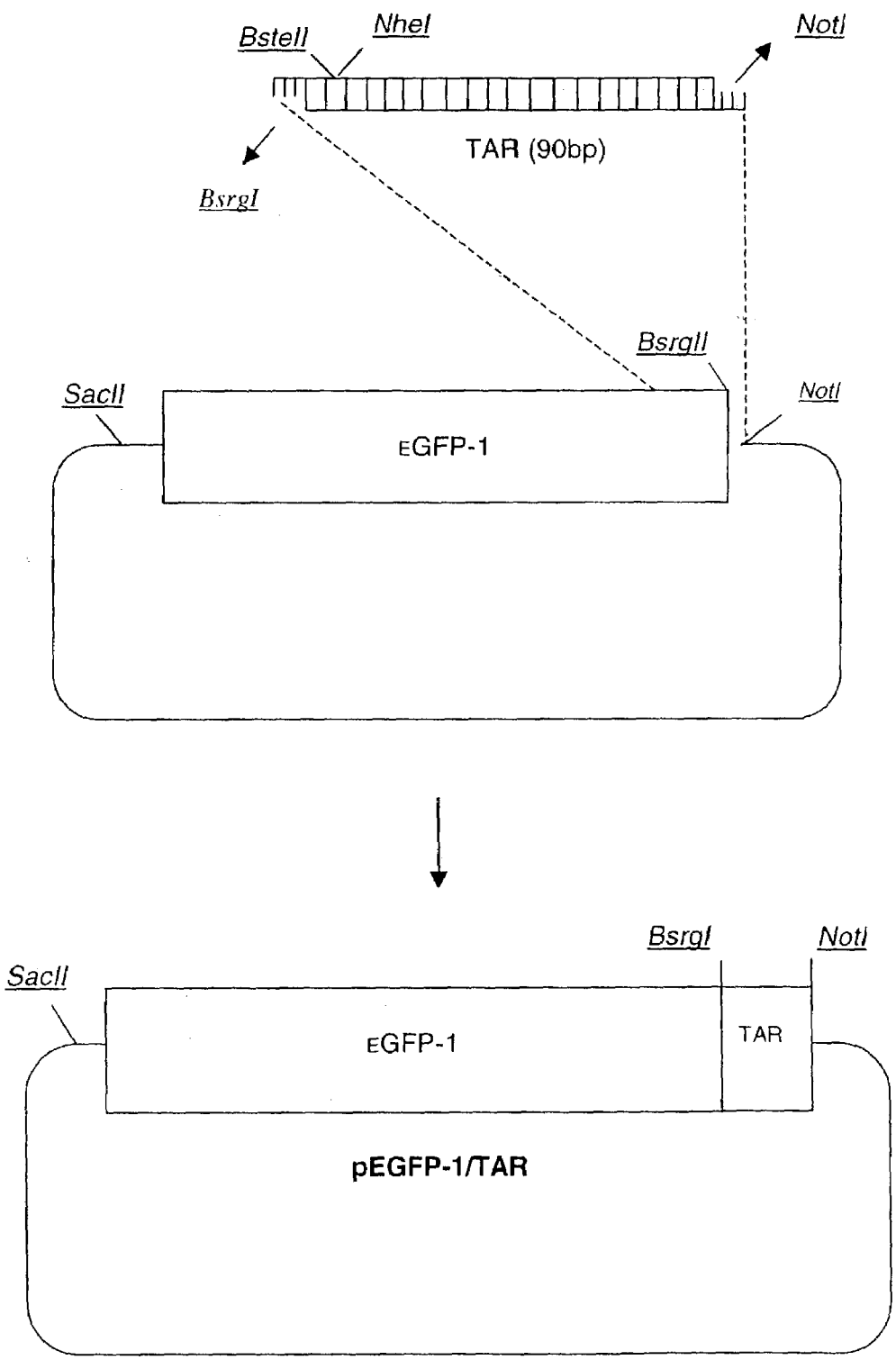
FIG. 10 shows the construction of pEGFP-1/TAR.

To make the heterologous insert, the starting point was plasmid pEGFP-1 (Clontech) digested with BsrgI and NotI. A dsDNA sequence with BsrgI (5') and NotI (3') cohesive ends and including the HIV-1 TAR sequence (nucleotides 454–520 HIV-1 genome, accession K03455) was obtained by annealing two complementary oligonucleotides, TAR-f and TAR-r, and this was inserted into the digested pEGFP-1 to form pEGFP-1/TAR (FIG. 10). The TAR oligo maintained the EGFP ORF and also included a translational stop codon just downstream from the BsrgI site, immediately followed by new BstEII and NheI restriction sites. A TAR sequence has also been successfully inserted upstream of the replicase ORF.

Figure 11:
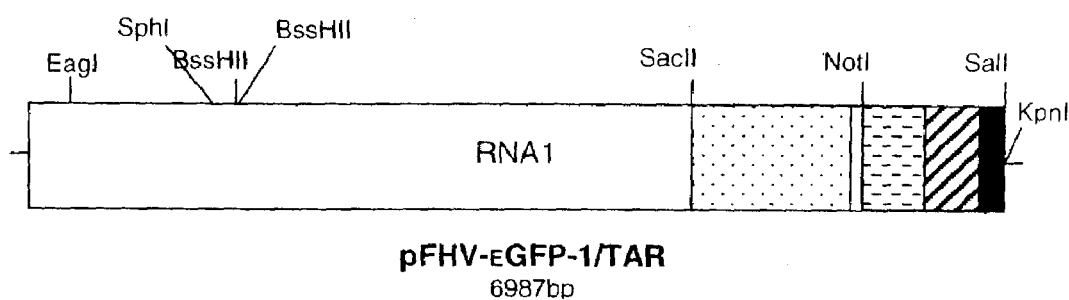
FIG. 11 shows pFHV-EGFP-1/TAR, with the TAR shown as horizontal dashes and the GFP coding region dotted.
Figure 12:
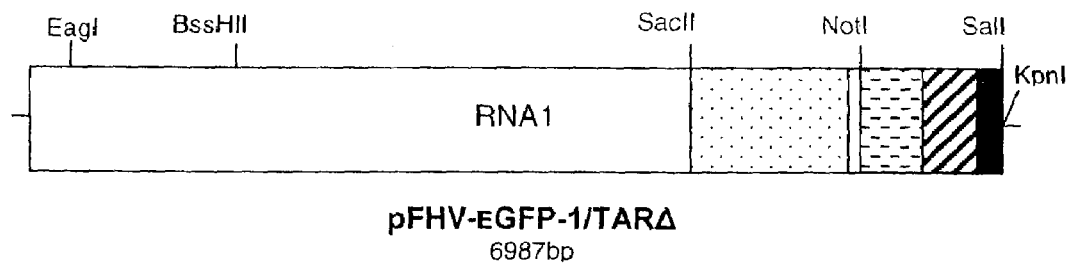
FIG. 12 shows pFHV-EGFP-1-TARΔ.

The SacII-NotI fragment from pEGFP-1/TAR, including the GFP coding sequence followed by the HIV-1 TAR sequence, was cloned in pFHV-Mut digested with the same restriction enzymes, obtaining a plasmid named pFHV-EGFP-1/TAR (FIG. 11). The SphI/SacII fragment of this plasmid was replaced with the corresponding fragment from pFHV-MutΔ (FIG. 6c), to generate pFHV-EGFP-1/TARΔ (FIG. 12) with only one BsshII restriction site.

Facilitating Expression of the Heterologous Insert

Polycistronic RNAs can be translated in mammalian cells by insertion of an internal ribosomal entry site (IRES) [Parks et al. (1986) *J. Virol.* 60:376–384] between the two genes of interest, thereby permitting cap-independent translation of the second (downstream) gene. To facilitate expression from the heterologous insertion, the IRES from encephalomyocarditis virus was thus inserted in front of the EGFP-1 gene. This IRES will typically provide translation of the EGFP protein only in mammalian cells, as IRES-mediated translation is selectively inhibited in yeast [Venkatesan et al. (1999) *Nucl. Acids Res.* 27:562–572.].

Figure 13:
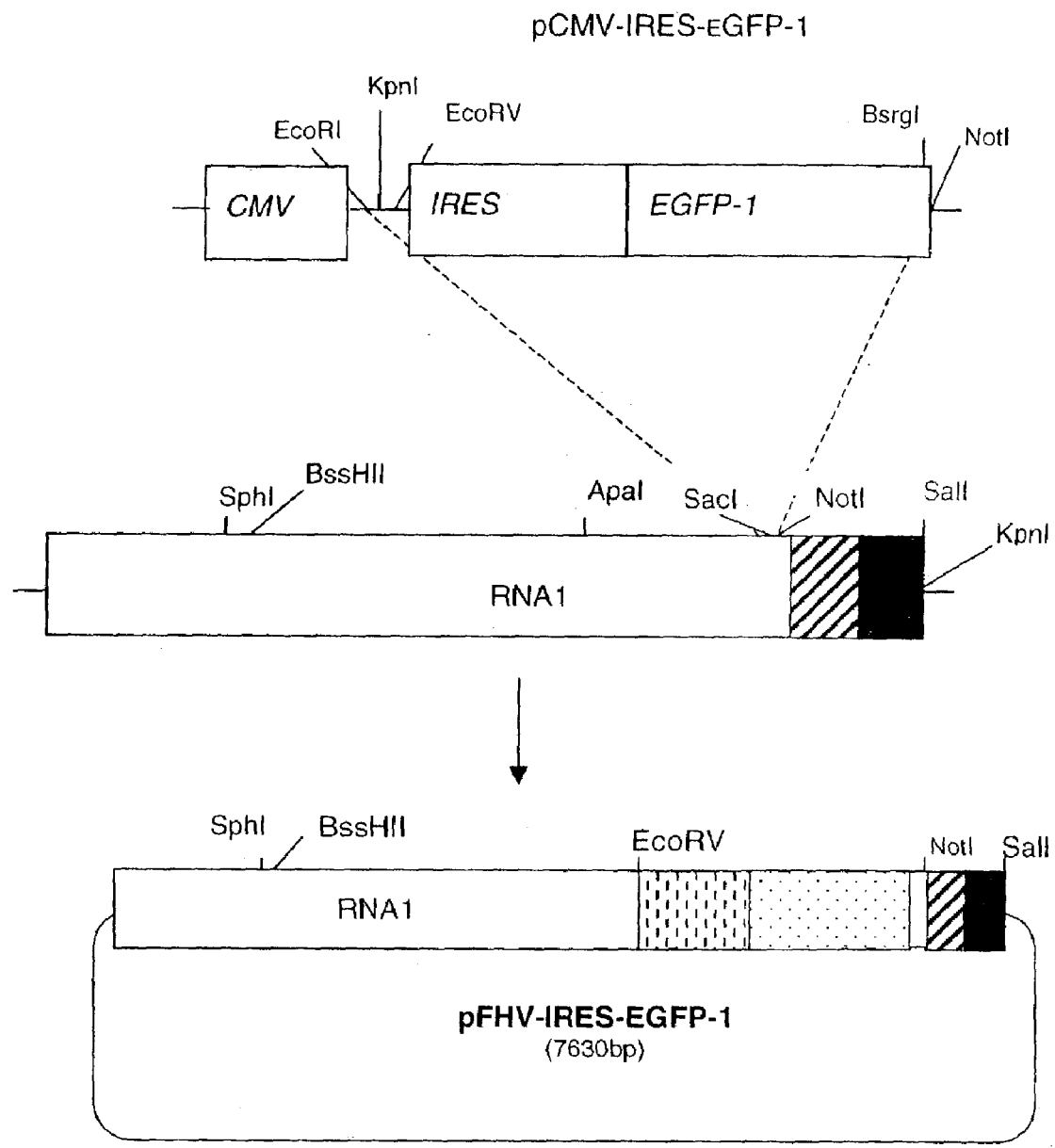
FIG. 13 shows the construction of pFHV-IRES-EGFP-1, with the IRES shown as vertical dashes.

Plasmid pCMV-IRES/EGFP-1 (FIG. 13) was digested with EcoRI, treated with klenow enzyme to blunt-end the site and, following inactivation of the enzymes, was digested with NotI, generating a 5' bluntended-3' NotI fragment containing the EMCV IRES fused to the EGFP-1 gene. Similarly the plasmid pFHV-MutΔ (FIG. 6c) was digested with SacII, treated with klenow enzyme and then digested with NotI. The IRES-EGFP-1 fragment was cloned into the digested plasmid, giving pFHV-IRES-EGFP-1 (FIG. 13).

Figure 14:
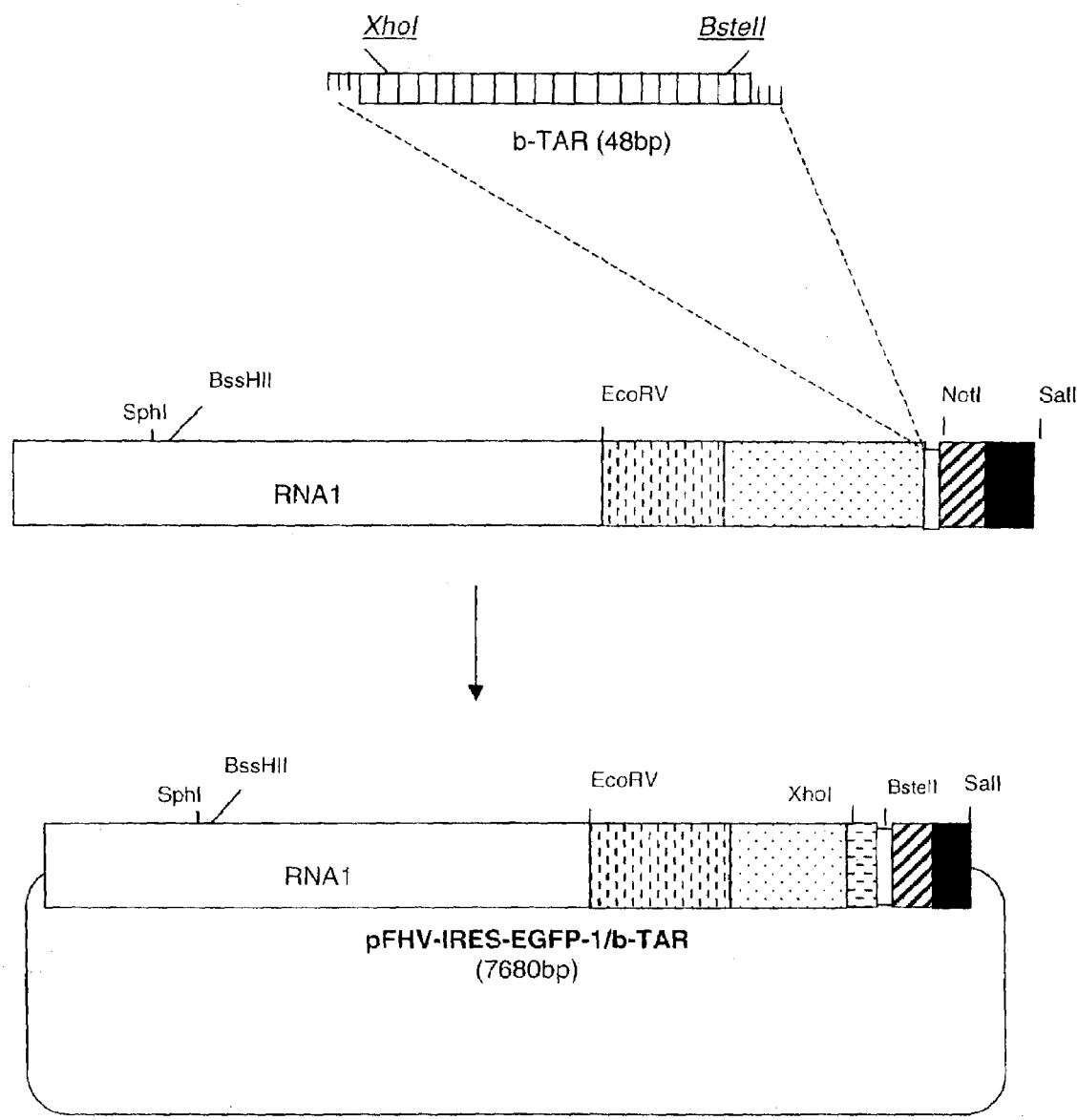
FIG. 14 shows the construction of pFHV-IRES-EGFP-1-b-TAR.

To assist in packaging RNA expressed from this construct, the TAR from BIV (nucleotides 5–30 BIV genome, accession M32690) was inserted downstream from the EGFP gene. The TAR sequence was constructed by annealing two complementary oligonucleotides (b-TAR-f and b-TAR-r) with NotI compatible cohesive ends. This also introduced two new restriction sites, BstEII (next to the 5' NotI site) and XhoI (next to the 3' NotI site). The double-stranded NotI fragment was cloned into NotI-digested pFHV-IRES-EGFP-1, to give pFHV-IRES-EGFP-1/b-TAR (FIG. 14). The correct orientation of the NotI fragment was confirmed.

Cloning into Yeast Expression Vectors

Four yeast expression plasmids were constructed with the following basic 5' to 3' layout: yeast specific promoter: modified RNA1; HDV ribozyme: T7 terminator, yeast polyA site.

Figure 15:
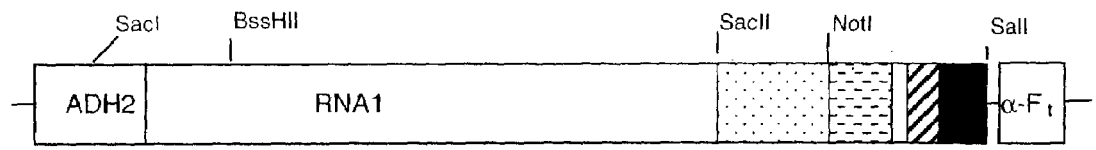
FIG. 15 shows pBS-ADH2-RNA1-EGFP-1 TARΔ (19.6 kb).
Figure 16:
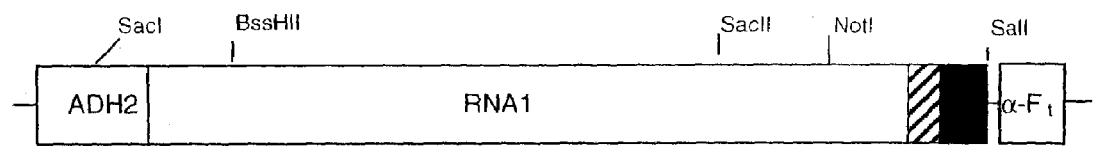
FIG. 16 shows pBS-ADH2-RNA1-MutΔ (18.1 kb).
Figure 17:
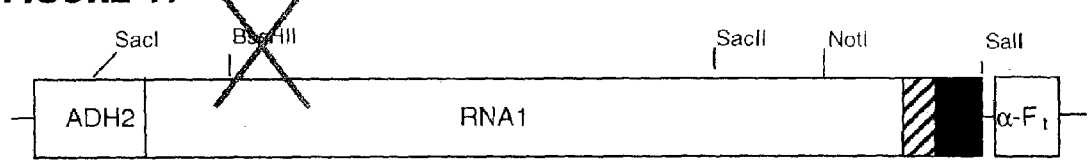
FIG. 17 shows pBS-ADH2-RNA1-MutΔ(–) (18.1 kb).
Figure 18:
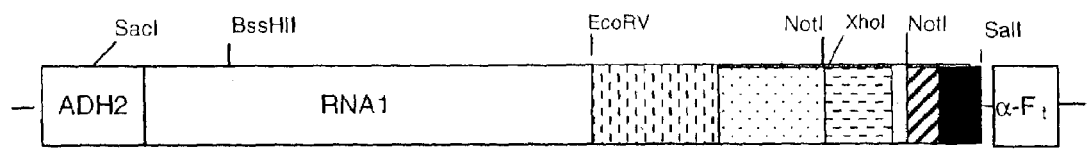
FIG. 18 shows pBS-ADH2-RNA1-IRES-EGFP-1/b-TAR (20.2 kb).

Initially, the SacI-BsshII fragment pBS24.1-6L1 (FIG. 8) was replaced with the corresponding fragment from pSK+-ADH2-RNA1/BsshIIΔ, to give plasmid pBS-ADH2-RNA1/BsshIIΔ-6L1, in which part of the RNA1 cDNA was fused to the 3' end of L1 gene sequence (not shown). This was manipulated as follows:

1. The BsshII-SalI L1 fragment was replaced with the BsshII-SalI fragment from pFHV-EGFP-1/TARΔ, giving pBS-ADH2-RNA1-EGFP-1/TARΔ (FIG. 15).
2. The BsshII-SalI L1 fragment was replaced with the BsshII-SalI fragment from pFHV-MutΔ, giving pBS-ADH2-RNA1-MutΔ (FIG. 16).
3. Filling in the unique BsshII site (1273) in pBS-ADH2-RNA1-MutΔ, with interruption of the replicase ORF, generated pBS-ADH2-RNA1-MutΔ (−) (FIG. 17).
4. Replacement of the BsshII-SalI fragment (including part of the modified RNA1 cDNA sequence) in pBS-ADH2-RNA1-MutΔ with the corresponding BsshII-SalI fragment (including IRES-EGFP-1/b-TAR) from pFHV-IRES-EGFP-1/b-TAR generated a plasmid named pBS-ADH2-RNA1-IRES-EGFP-1/b-TAR (FIG. 18).

Yeast Transformation

Plasmids pBS-ADH2-RNA1-EGFP-1 TARΔ. pBS-ADH2-RNA1-MutΔ. pBS-ADH2-RNA1-MutΔ (−) and pBS-ADH2-RNA1-IRES-EGFP-1/b-TAR (FIGS. 15–18), were introduced by transformation into a AB110 strain previously obtained in the laboratory (WO00/09699) and which expresses HPV-16L2 protein. The resulting strains were named pBS-RI-G/TΔ (clones 4 and 5 selected). pBS-RI-MutΔ (clones 1 and 3 selected). pBS-RI-MutΔ (−) (clones 5 and 7 selected) and pBS-RI-IRES-G/b-TAR (clones 5 and 9 selected), respectively.

Confirmation of Self-replication

Confirmation of RNA replication. Total RNAs were extracted from strains pBS-RI-MutΔ. pBS-RI-MutΔ (−) and pBS-RI-IRES-G/b-TAR and labelled as RepA(+). RepA(−) and RepA(+)-GFP respectively. These RNAs, together with a negative control RNA from the AB110 strain labelled as c-, were analysed by Northern blot using a non radioactive (BrighStar Psoralen-Biotin labelling kit, Ambion) DNA probe (600 bp) obtained by PCR carried out on pFHV[1,0] using primers ApaI-f and repA-Rev.

Figure 19:
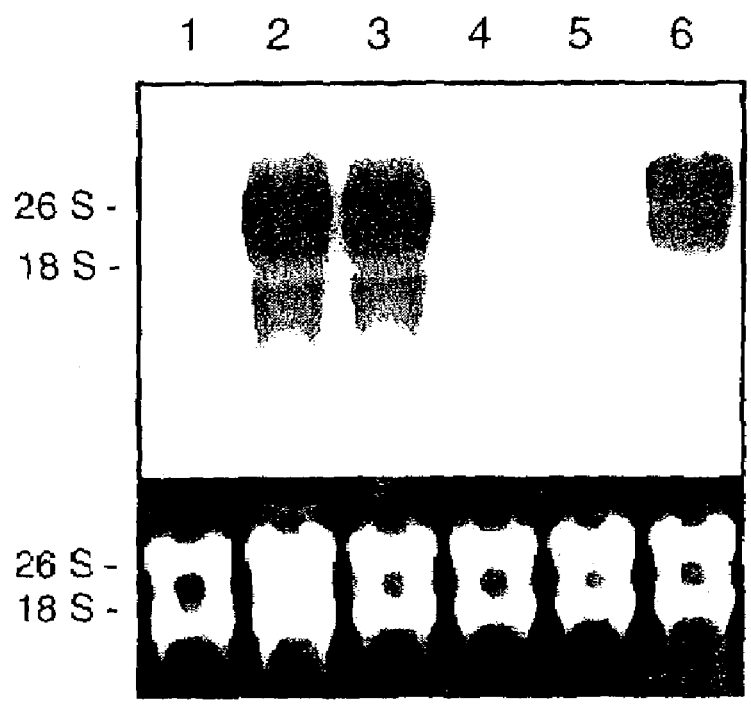
FIG. 19 shows a Northern blot of total RNA from yeasts transformed with the vectors of FIGS. 16–18. Lane 1 shows a negative control (total RNA from AB110): lane 2 is RepA(+) clone 5; lane 3 is RepA(+) clone 7; lane 4 is RepA(–) clone 3: lane 5 is RepA(–) clone 4: lane 6 is RepA(+)-GFP. Yeast rRNA 26S (2250 bp) and 18S (1650 bp) are also shown.

FIG. 19 shows the results, indicating that high hybridization signals are only detected with RNAs extracted from yeast clones designed to express the replicase ORF, both when the RNA1 sequence has no insertions (lanes 2 and 3) and when the IRES-EGFP/bTAR sequence is introduced downstream from the replicase and B2 ORFs (lane 6). A much weaker signal is detected with RNAs from yeast clones transformed with a plasmid where the replicase ORF is interrupted (lanes 4 and 5), while no signal is detected with the negative control RNA.

These results confirm that the replicase can sustain self-replication of RNA1 even when a heterologous insert (foreign gene) is introduced in the wild type RNA1 sequence.

Figure 20:
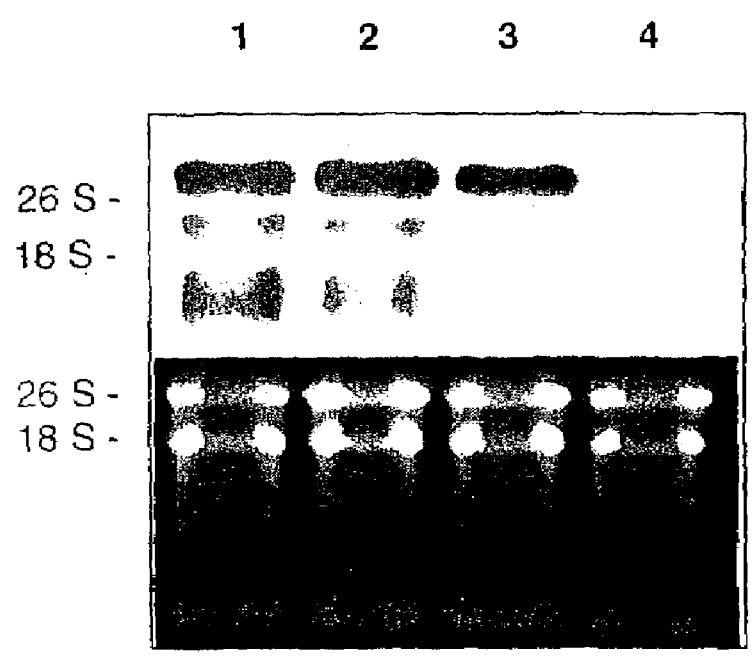
FIG. 20 shows a Northern blot for EGFP-1 of total RNA from yeasts transformed with the vector of FIG. 18. Lane 1 shows RNA extracted from a 24 hour induced culture: lane 2 is after 48 hours: lane 3 is after 72 hours: lane 4 is a negative control (total RNA from AB110).

To confirm that the self-replicating modified RNA1 did contain the IRES-EGFP/b-TAR sequence, a Northern blot was performed using a non radioactive DNA probe of the entire EGFP region. The experiment confirmed expression of the recombinant RNA1 at 24, 48 and 72 hours (FIG. 20).

Confirmation of Protein Expression

As well as confirming self-replication at the RNA level, protein expression was also assayed using anti-replicase antibodies.

To obtain anti-replicase antibodies, the C-terminal portion of the replicase (DVWEK . . . SNNRK, referred to as RepApep (SEQ ID NO: 1)) was expressed in *E. coli*. This protein includes the complete B1 protein so, advantageously, anti-RepApep antibodies should detect B1 expression as well as replicase. The same region was also expressed with a +1 frameshift to obtain bacterially expressed B2 protein. Detection of B1 or B2 proteins would confirm self-replication.

The RepApep portion of the replicase ORF was PCR amplified using primers RepA-dir and RepA-rev containing NheI (5') and XhoI (3') restriction sites. The PCR blunt-ended product was cloned into pCR-BluntII-TOPO (Invitrogen) and the sequence of the inserts from different clones was checked. The NheI(5')-XhoI(3') fragment was extracted from one of the correct clones by digestion with the two restriction enzymes and was cloned into pTrc-HisA (Invitrogen), generating a plasmid named pTrc-RepApep-His$_6$ containing an ORF where the RepApep was in frame with a hexahistidine tag (FIG. 21a).

The entire B2 ORF was amplified by PCR using primers B2-dir and B2-rev containing the same NheI and XhoI sites. The PCR product was digested with the two enzymes and directly cloned into pTrc-HisA (Invitrogen), generating a plasmid named pTrc-B2-His$_6$ containing an ORF where the B2 was in frame with a hexahistidine tag (FIG. 21b).

Figure 23:
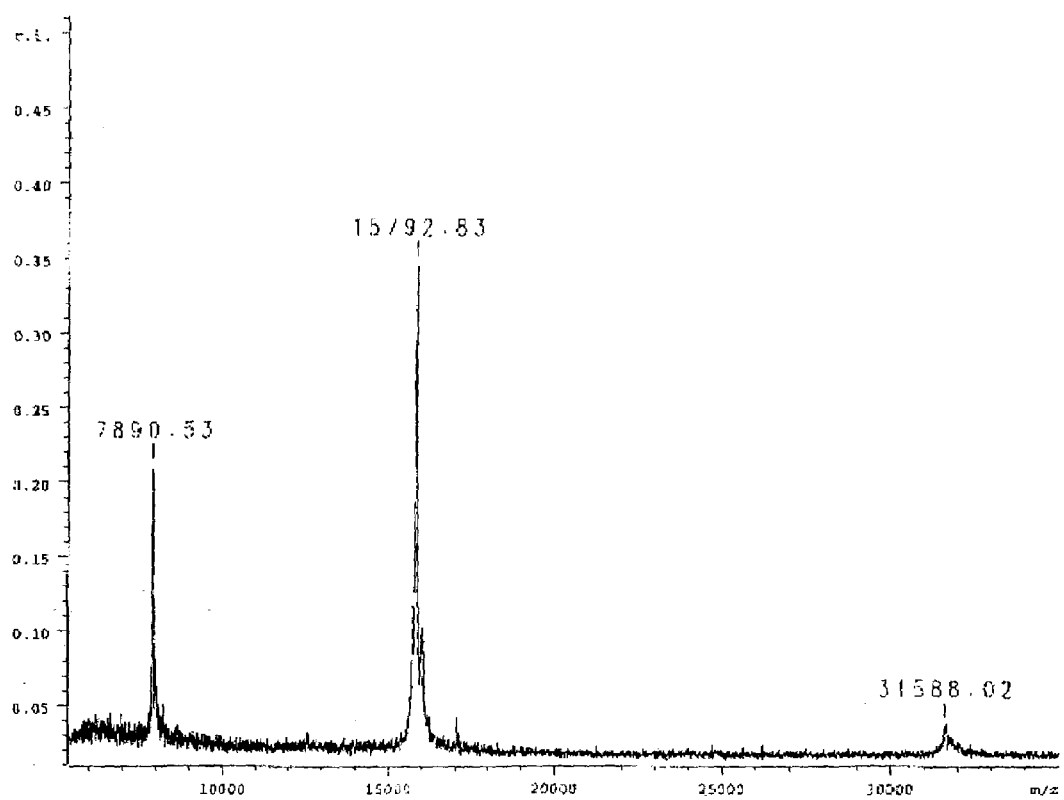
FIG. 23 shows mass spectrometry of RepApep.

Total soluble protein extracts from bacterial clones expressing either of the two recombinant proteins were subjected to IMAC using Ni-NTA resin (Hoffmann-La Roche) and fractions enriched for RepApep and B2 protein were collected (FIG. 22). The RepApep protein showed an unexpected migration profile in SDS-PAGE, so the purified protein was subjected to mass spectrometry (FIG. 23) which confirmed the expected 15–16 kDa MW.

Fractions containing the enriched protein were pooled, dialysed against PBS, and protein content was measured with a BCA test (Pierce). The proteins were used to immunise groups of 5 mice either 3 times (repApep, 50 μg/dose) or 4 times (protein B2, 25 μg/dose) at two week intervals. Vaccines were administered intraperitoneally (IP) using 200 μl of antigen and the same volume of MF59 [Ott et al. (1995) pages 277–296 of *Vaccine design*. The subunit and adjuvant approach (eds. Powell & Newman) Plenum Press]. Pre-immune sera were collected prior the immunization and serum samples were taken two weeks after each immunization.

Figure 24:
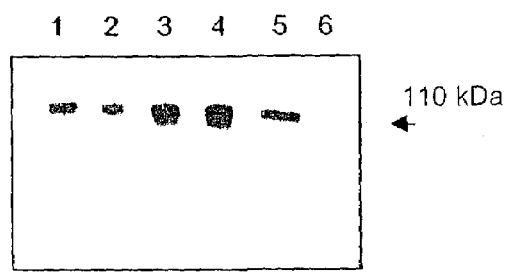
FIG. 24 is a western blot of total protein extracts from yeasts transformed with the sector of FIG. 15. Lanes 1 to 5 are extracts immunoreacted with sera from five immunised mice at 1:5000 dilution: lane 6 is a negative control, comprising a mix of pre-immunisation sera.

Serum samples of the 5 mice immunised with RepApep were tested at 1:5000 dilution on total protein extracts prepared from the yeast strain pBS-RI-G/TΔ (clone 4), and detection of a ~110 kDa protein was observed in all of them, in agreement with the existence of yeast expressed replicase (FIG. 24).

Figure 25:
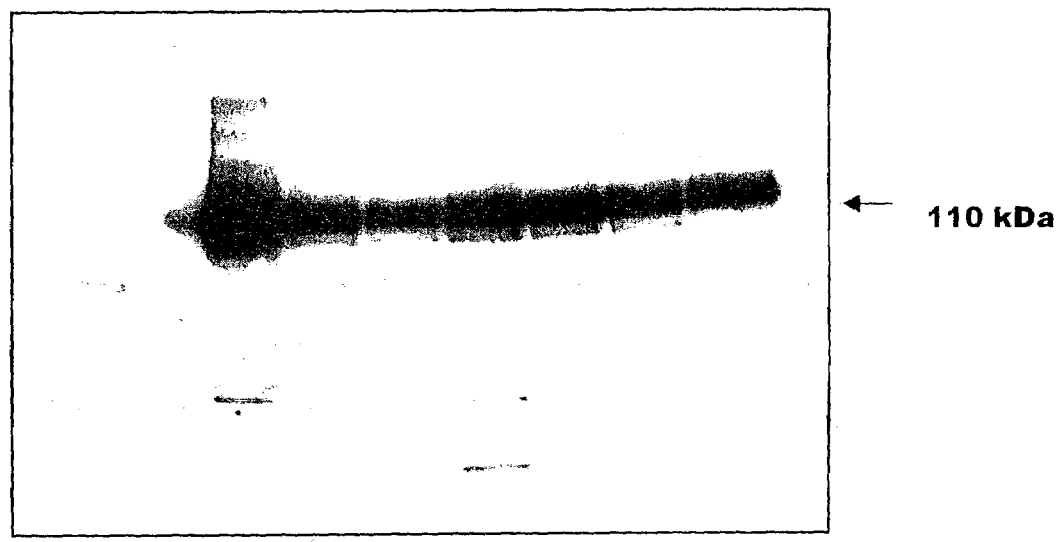
FIG. 25 is a western blot of total protein extracts from various yeast strains over a 72 hour period. Lane 1 is a negative control; lane 2 is a total protein extract from pBD-R1-G TΔ clone 5 at 48 hours: lanes 3 to 5 are total protein extracts of RepA(+)-GFP strains, clone number 7, at 24, 28 and 72 hours: lanes 6 to 8 show the same for clone number 9.

The same dilution of the serum used in lane 4 of FIG. 24 was used for a Western blot analysis on total protein extracts from different yeast strains grown under inducing conditions for variable time periods. The experiment confirmed that the RNA1 replicase is present at 24, 48 and 72 hours in strains expressing the modified RNA1 (FIG. 25).

Figure 26:
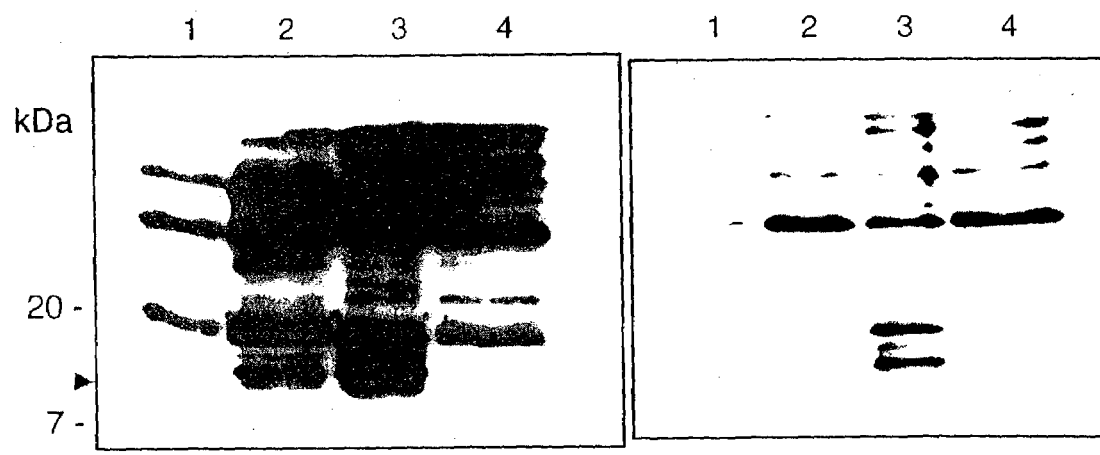
FIG. 26 is a western blot of total protein extracts from RepA(+)-GFP strains. Lane 1 is a negative control (total protein extract from AB110). Lane 2 shows protein from a 24 hour induced culture; lane 3 is after 48 hours; lane 4 is after 72 hours.

The serum used in lane 4 of FIG. 24 was used for a Western blot analysis on total protein extract prepared at 24, 48 and 72 hours induction from the yeast strain carrying pBS-RI-G/TΔ (FIG. 26). A protein band (lanes 2 and 3) was detected between the 20 kDa and the 7 kDa MW markers which is not present in the negative control extract (lane 1) and in the extract prepared after a 72 hour induction (lane 4). This is in agreement with the synthesis of B1 protein in yeast, again confirming self-replication of the modified RNA1. The absence of B1 protein at 72 hours is in agreement with the B1 and B2 expression data previously obtained in mammalian cells [Johnson & Ball (1999) *J. Virol.* 73:7933–7942].

Confirmation of RNA3 Expression

Figure 30:
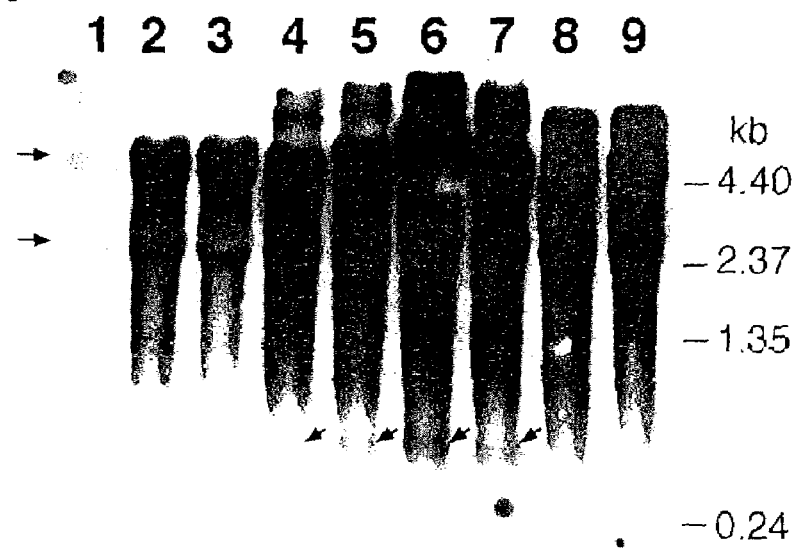
FIG. 30 shows a Northern blot of total RNA from yeast strains RepA (–) lane 2 grown 24 hr. lane 3 grown 48 hr), two different RepA(+) strains (lanes 4 and 5 grown 24 hr. lanes 6 and 7 grown 48 hr) and strain RepA(+)-IRES-EGFP/bTar (lane 8 grown 24 hr. lane 9 grown 48 hr). A negative control RNA (lane 1) and RNA molecular weight markers are also shown. Arrows indicate the position of the signals corresponding to RNA3.
Figure 31:
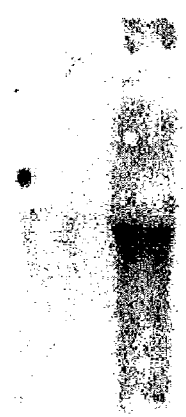
FIG. 31 shows a Northern blot of the RNAs from (1) lane 3 and (2) lane 6 of FIG. 30.

Total RNAs were extracted from yeast strains expressing the plasmids pBS-ADH2-RNA1MutΔ(−). pBS-ADH2-RNA1MutΔ and pBS-ADH2-RNA1-IRES-EGFP-1/b-Tar, grown for 24 and 48 hours and labelled as RepA(−), RepA(+) and RepA(+) IGFP/b-Tar, respectively. These RNAs were analysed by Northern blot analysis using the non radioactive double stranded DNA probe as for FIG. 19. FIG. 30 shows that overexposing the film reveals a weak signal corresponding to a RNA species migrating as expected for RNA3 is detected both at 24 and 48 in the strain RepA(+) (lanes 4 to 7). A Northern blot was performed using the RNA from lane 6 over a longer time period on agarose gel and the filter was cut before hybridisation to include only the area were RNA3 was present (FIG. 31). This confirms the existence of RNA3. In the case of RNA derived from the strain RepA(+) IGFP/b-Tar (FIG. 30, lanes 8 and 9), the corresponding RNA3, which would migrate slower due to the insertion, could not be observed, presumably masked by the intense RNA1 hybridisation signal.

Confirmation of RNA Minus Strand

Figure 32:
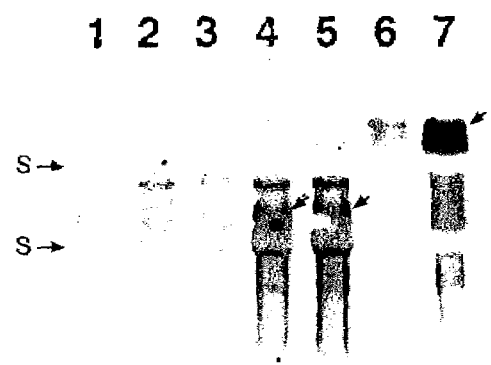
FIG. 32 shows a Northern blot as described for FIG. 30, but using a different probe. Arrows indicate the position of the signals corresponding to RNA1 minus strand.

RNAs extracted from strains RepA(−), RepA(+) and RepA(+) IGFP/b-Tar grown at 24 and 48 hours were analysed by Northern blot using a strand specific non-radioactive probe(BrighStar Psoralen-Biotin labelling kit. Ambion to detect the RNA minus strand. The strand specific probe was an in vitro transcript obtained by using the plasmid pFHV-MutΔ linearised with SacII. FIG. 32 shows that a strong hybridisation signal corresponding to RNA of the expected size is detected only in clones expressing the replicase protein, both when the RNA1 sequence has no insertions (lanes 4 and 5) and when the IRES-EGFP/b-Tar sequence is introduced downstream from the B2 ORF (lanes 6 and 7). No signal is detected in control RNA (lane 1) and when the replicase ORF is interrupted (lanes 2 and 3).

Primer Extension and S1 Mapping Analysis of RNA1

Standard primer extension analysis was carried out on total RNAs from strains RepA(−). RepA(+) and RepA(+) IGFP/b-Tar using AMV reverse transcriptase and the T4 kinase labelled oligonucleotide R1-120

Figure 33:
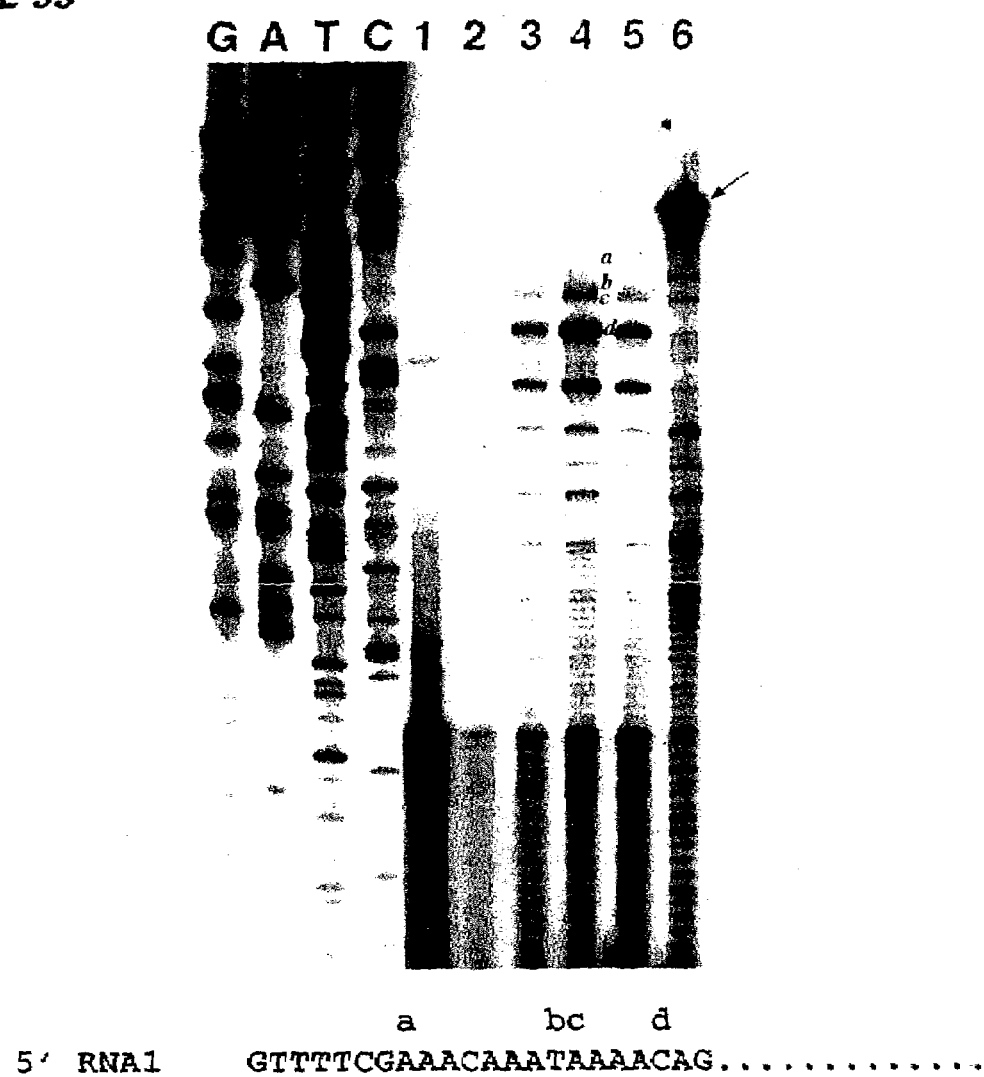
FIG. 33 shows a primer extension experiment on total RNA from 48 hr grown yeast strains RepA(–) (lane 2), RepA(+) (lane 3), RepA(+) EGFP/hTar (lane4) and RepA (+)-IRES-EGFP/bTar (lane 5). A negative control RNA (lane 1) and a positive control on in vitro transcribed RNA1 (lane 6) are also reported. Letters a, b, c and d in lane 4 identify bands (three of them also visible in lanes 3 and 5) which correspond to the nucleotides indicated on the RNA1 5' sequence (SEQ ID NO: 4).

The extension products were run on a 8% denaturing polyacrylamide/urea gel with a control sequence carried out on plasmid pSK+-ADH2-RNA1/SpeI (FIG. 7f) by using the same primer. FIG. 33 shows that shorter extension products can be detected.

S1 mapping analysis was carried out using the same RNAs. The probe was a double-stranded PCR fragment obtained from plasmid pSV40-FHV [0,0] using oligos AZ15-for (nt 6285 in the plasmid) and R1-120. The PCR fragment was labelled with T4 kinase, digested with NcoI to remove the radioactive label from the strand which had the same polarity of the mRNA to be detected, and gel purified. Aliquots of the radioactive probe were hybridised to total RNAs and digestion with S1 nuclease was carried out under standard conditions. As a control, a T7 in vitro transcribed RNA1 from pFHV [1,0] was also hybridised to the probe and S1 digested. The S1 treated products were run on a 8% denaturing polyacrylamide/urea gel along with a DNA sequence obtained by using the primer R1-90rev and complementary to RNA1.

Figure 34:
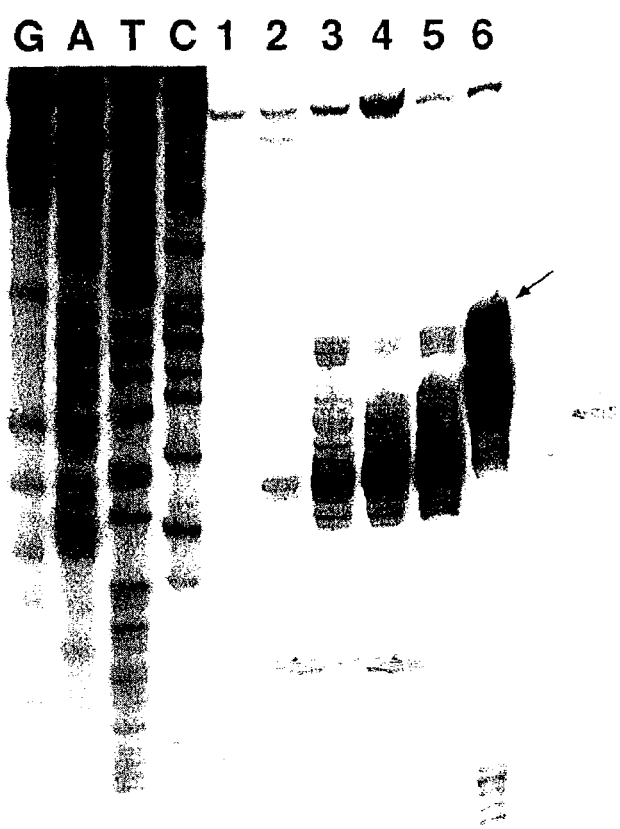
FIG. 34 shows a S1 mapping experiment using the same total RNAs reported in FIG. 33. The results of S1 reactions using a negative control RNA (lane 1) and a positive control on in vitro transcribed RNA1 (lane 6) are also reported.

As shown in FIG. 34, bands corresponding to full-length RNA can be detected in samples expressing the replicase A without or with GFP and IREs-GFP insertions (lanes 3, 4 and 5).

Cloning and Sequencing of the 5' End of RNA1

Total RNA derived from the strain RepA(+)-IGFP/b-Tar was used to clone the 5' end of the RNA1 species. Cloning was carried out by using the Ambion FirstChoice™ RLM-RACE Kit, which allows selective cloning of capped mRNA molecules. The primers used were:
1) Reverse transcription with R1-rev
2) Outer PCR with the outer RNA adapter primer supplied with the kit and reverse primer AZ-9rev (nt 426 on RNA 1)
3) Inner PCR with the inner RNA adapter primer supplied with the kit and R1-120.

Cloning of the final PCR product was carried out into pZero blunt vector (Invitrogen). Sequencing of 10 clones revealed that the cloned sequence of all of them began AAAACAG (nucleotide 16 of RNA1 sequence). This corresponds to product c shown in FIG. 33. Band d in FIG. 33 may thus represent a degradation product of c, and band b may be a capped form.

Cloning and Sequencing of the 5' End of RNA3

Using the same experimental procedures, the 5' region of RNA3' was cloned from the same yeast clones. The primers used were:
1) Reverse transcription with AZ-5rev (nt 3101 of RNA1)
2) Outer PCR with the outer RNA adapter primer supplied with the kit and reverse primer AZ-5rev
3) Inner PCR with the inner RNA adapter primer supplied with the kit and R3-2809rev (nt 2830 on RNA1).

The final PCR products were digested with NcoI (nt 2801 on RNA1) and BamHI (within inner adapter primer) and cloned in pTRC-HisB (Invitrogen) digested with the same enzymes.

Sequencing of 10 clones from RT-PCR carried out with RNA from the RepA(+) strain revealed that same sequence in each case, beginning at nucleotide 2721 of RNA1 (GTTACCAA . . . ). This corresponds to the RNA3 start site already reported in the literature.

Sequencing of 18 clones from RT-PCR carried out with RNA from the RepA(+)-IGFP/b-Tar strain revealed that none corresponds to the RNA3 transcriptional start site, but all of them initiate with upstream sequences belonging to RNA1.

Packaging in HPV VLPs

To promote packaging of the modified RNA1 carrying a TAR insert, the L1 coat protein of HPV-6 was modified to include a complementary tat motif at its C-terminal.

Figure 27:
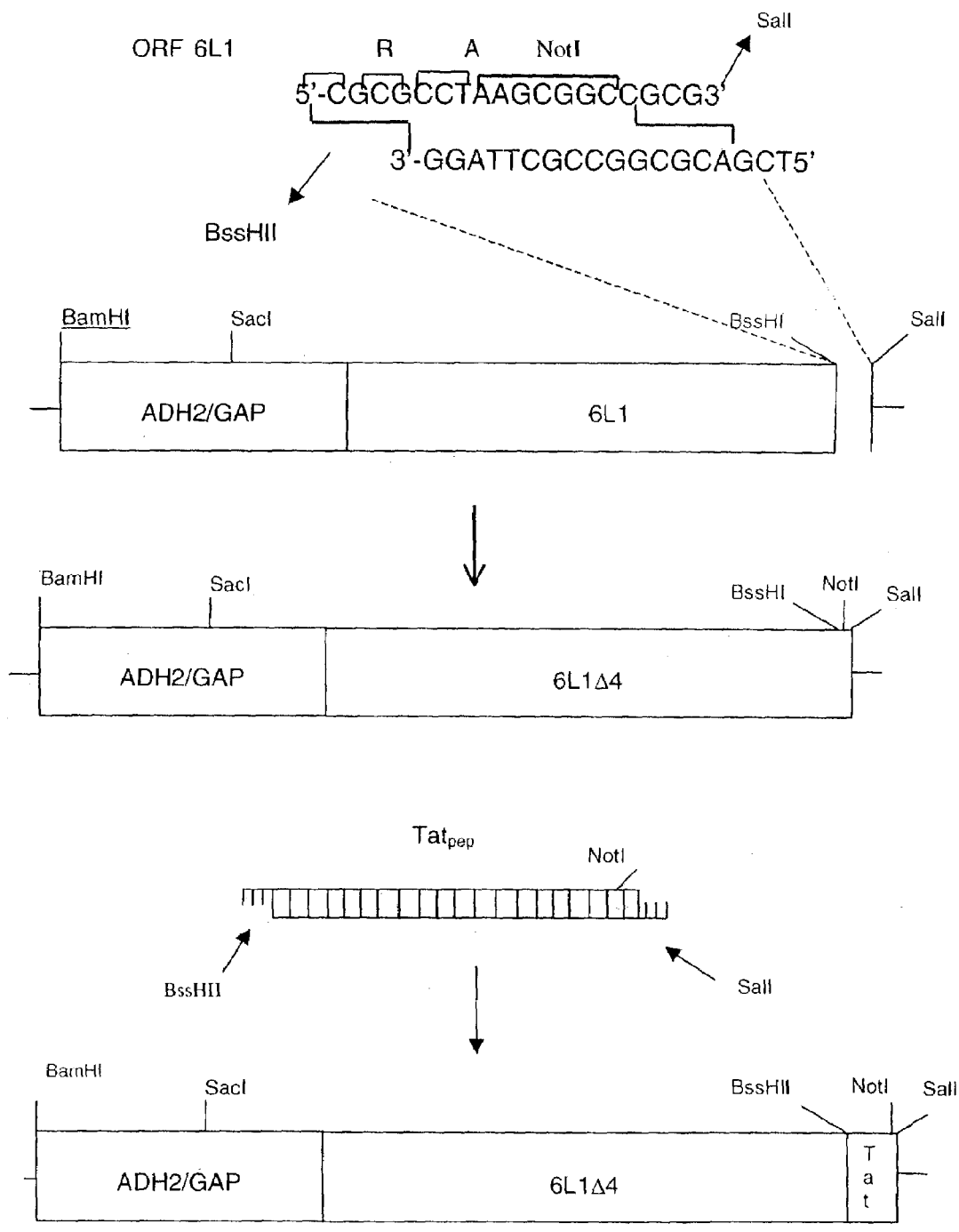
FIG. 27 shows the construction of pBS-ADH$_2$/GAP-6L1 4-Tat. ORF 6L1 primers are shown as SEQ ID NO: 33 and 21, respectively.

The construction of the yeast expression vector to achieve this included several steps (FIG. 27). Firstly, plasmid pBS24.1-6L1 (FIG. 8) was digested with BsshII and SalI, thus eliminating the last 4 amino acids of the L1 protein. This plasmid expresses HPV-6 L1 capsid protein in yeast. A short BsshII-SalI dsDNA, obtained by annealing complementary oligonucleotides 6L1Δ4 and 6L1Δ4inv, was inserted, thereby reconstituting the L1 ORF, giving it a translational stop codon and a new NotI restriction site. The resulting yeast expression plasmid was named pBS24.1-6L1Δ4. PCR amplification of the HIV-1 TAR-binding domain of tat (amino acids 36 to 72) was carried out on a plasmid containing the cDNA of HIV-1 strain IIIB by using the primers Tat-dir and Tat-rev, which also included a BsshII site at the 5' end and NotI and SalI sites at the 3' end. The resulting blunt-ended fragment was cloned into pCR2.1 plasmid and sequenced. The BsshII-SalI fragment was extracted from pCR2.1 and ligated with pBS24.1-6L1Δ4 digested with the same restriction enzymes. The resulting plasmid was named pBS24.1-6L1Δ4-Tat.

pBS24.1-6L1Δ4-Tat was introduced by transformation into a JSC310 strain previously obtained in the laboratory (WO00/09699) and which expresses HPV-6L2 protein. Different clones from the transformation experiments were analyzed for 6L1Δ4-Tat expression and clone 2 was selected for further experiments.

Figure 28:
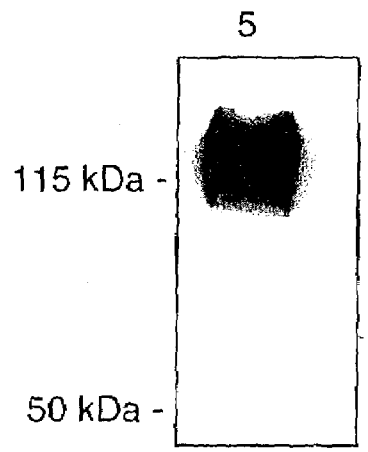
FIG. 28 shows a western blot on CsCl-purified 6L1Δ4-tat protein under non-reducing conditions using anti-6L1 (1:5000).

Clone 2 was grown under inducing conditions and cesium chloride (CsCl) gradient purification of VLPs was carried out as described in WO00/09699. The CsCl fraction corresponding to a density of 1.28–1.29 g/cm$^3$ was run under non reducing conditions on SDS-PAGE and analysed by Western blot using an anti-6L1 antibody (FIG. 28). The detection of a band which migrated slower than the 115 kDa Mw protein marker indicates that disulphide bonds among different L1/Tat monomers are formed, which is a known requirement for efficient self-assembly of HPV VLPs [Sapp et al. (1998) *J. Virol.* 72:6186–89].

Figure 29:
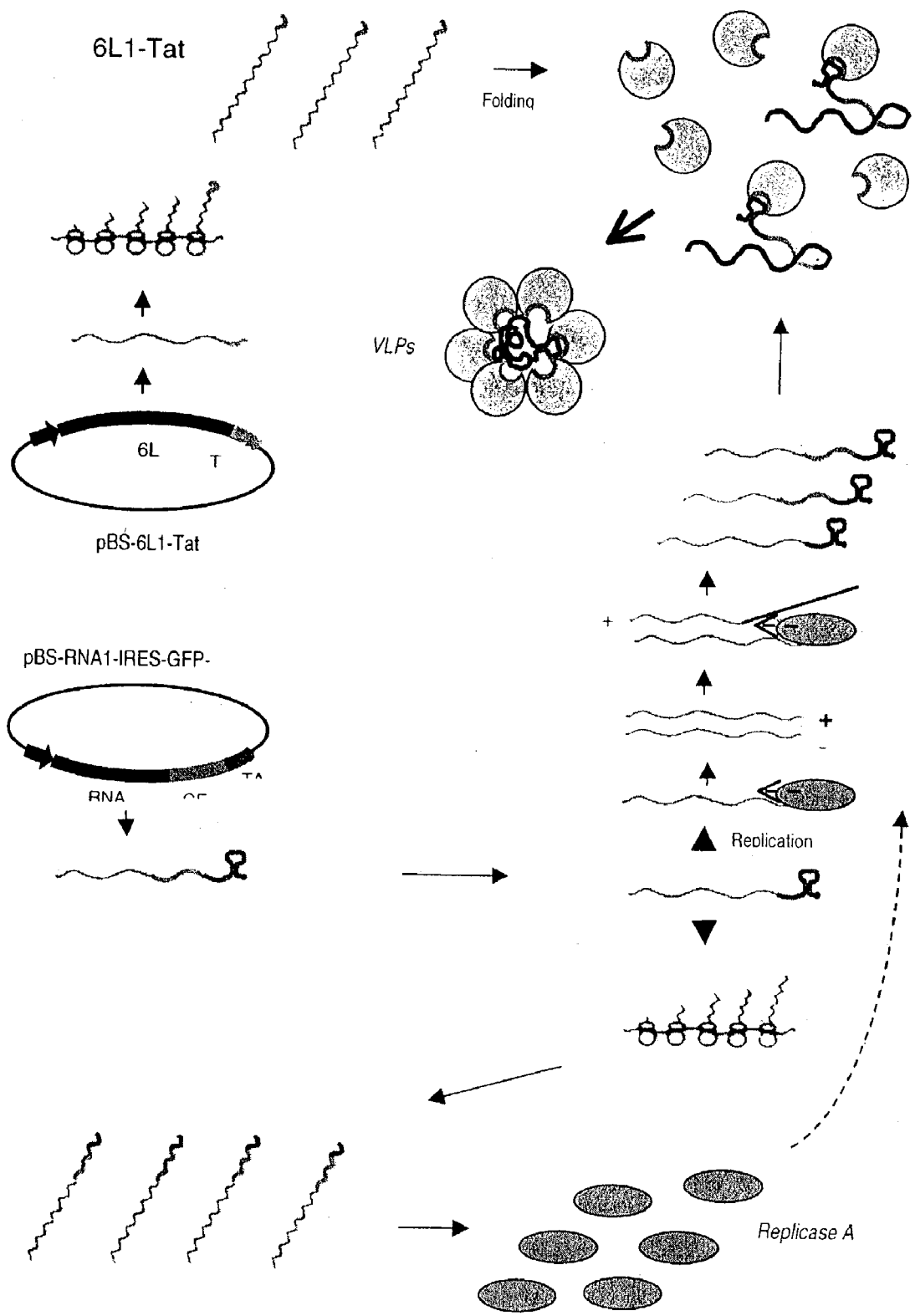
FIG. 29 illustrates the expression and packaging of modified RNA1 in VLPs in yeast.

The expression of replicase, self-replication of modified RNA1 carrying a TAR insert, expression of L1-Tat, and packaging of modified RNA1 is illustrated in FIG. 29. All steps take place in the same yeast cell, resulting in infectious VLPs for delivering a gene of interest to mammalian cells.

Yeast strain JSC310 containing the plasmid pBS24.1-6L1Δ4-Tat, clone 2, was mated with strain AB110 containing the plasmid pBS-ADH2-RNA1-EGFP-1/TARΔ to obtain a diploid clone co-expressing the recombinant RNA1 derivative (containing the GFP gene and the human TAR sequence) and the recombinant HPV6 L1/hTAT protein. Different clones from the mating experiment were tested for L1 and replicase A protein expression and for RNA1-EGFP-1/TAR transcript levels. One diploid clone was chosen and grown under inducing conditions. CsCl gradient purification of VLPs was carried out as described in WO/00/09699.

Figure 35:
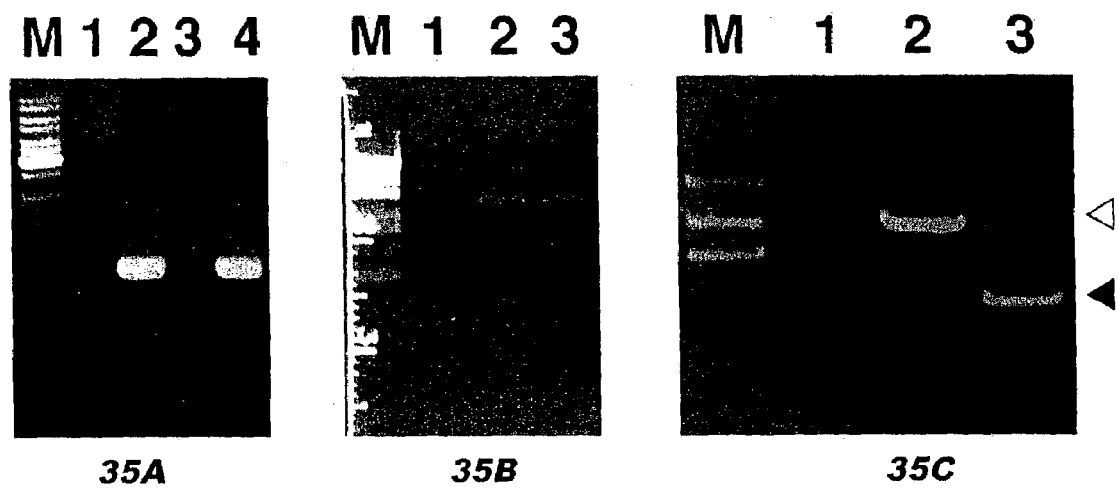
FIG. 35 shows the results obtained by RT-PCR using nucleic acids extracted from diploid HPV-6VLP co-expressing RNA1-IRES-GFP/hTar and HPV-6 L1/hTAT. 35A shows yeast control RNA (lanes 1 and 3) and VLP-derived nucleic acids (lanes 2 and 4); 35B shows yeast RNA (lanes 1) and nucleic acids derived from VLPs either untreated (lane 3) or treated with Benzonase (lane 2); 35C shows yeast RNA (lanes 1) and nucleic acids derived from VLPs either untreated (lane 3) or treated with RNAse A (lane 2) in the presence of mouse RNA as internal control.

The CsCl fractions corresponding to a density of 1.28–1.29 g/cm$^3$ were pooled and dialysed against PBS. The dialyzed VLPs were used for different experiments carried out following different procedures and reported in FIG. 35.

In FIG. 35A, the VLPs were treated with phenol, phenol-chloroform, chloroform and ethanol precipitated to obtain a material devoid of proteins. Aliquots of the final nucleic acids pellet suspended in water were subjected to RT-PCR without any additional treatment by using the OneStep RT-PCR kit (Qiagen) following the kit instructions. The primer used were R1–235 for (nt 235 on RNA1) and R1–1272M-r, resulting in the expected 1037 nt band (lanes 2 and 4, which are the same sample repeated in two different RT-PCR analysis). Unrelated yeast RNA was included as a control.

In FIG. 35B, a 100 μl aliquot of the pooled VLPs was subjected to a 24 hr treatment at 37° C. with 25 units of Benzonase (Merck) before the fenol/chlorophorm extraction. The final nucleic acids pellet was subjected to RT-PCR using the same primers as before. The 1037 nt band is observed, both when the VLPs had been previously treated with Benzonase (lane 2) and without any Benzonase treatment.

In FIG. 35C, a 100 μl aliquot of the pooled VLPs was subjected to a 1 hr treatment at 37° C. with 1 μg RNAse A before the phenol/chloroform extraction. Total mouse RNA was included in the sample as internal control of the RNAse treatment. Following phenol/chloroform extraction, the final nucleic acids pellet was subjected to RT-PCR by using two different sets of primers, the two RNA1 primers used for FIG. 35A and two primers amplifying an ~600 nt long band corresponding to mouse GAPDH mRNA. While the RNA1 band (empty arrow) is visible both when the VLPs had been previously treated with RNAse (lane 2) and without any RNAse treatment (lane 3), GAPDH mRNA can be amplified (black arrow) from the untreated sample (lane 3) and it is barely visible after RNAse treatment.

It will be understood that the invention has been described by way of example only and modifications may be made whilst remaining within the scope and spirit of the invention.

TABLE I primers

| NAME | SEQ ID NO | SEQUENCE (5'-3') |
|---|---|---|
| ADH-SAC | 2 | CCCAATTCGTCTTCAGAGCTCATTGTTTG (Sacl) |
| P-R1-rev | 3 | TTGTTTCGAAAACTAGATTTACAGAATTACAATCAATACCTACCGTC (underlined sequence corresponds to RNA1) |
| RNA1-t | 4 | GTTTTCGAAACAAATAAAACAGAAAAGCGAAAC |
| RNA1-r | 5 | TGAGCATGCTCCCCTTCTGGACC (Sphl) |
| TAR-f | 6 | GTACAAGTAAGGTTACCGCTAGCGGGTCTCTCTGGTTAGACCAGATCTGAGC CTGGGAGCTCTCTGGCTAACTAGGGAACCCACTGCTTAGC (BstEll and Nhel) |
| TAR-r | 7 | GGCCGCTAAGCAGTGGGTTCCCTAGTTAGCCAGAGAGCTCCCAGGCTCAGA TCTGGTCTAACCAGAGAGACCCGCTAGCGGTAACCTTACTT (Bstell and Nhel) |
| DRS-f | 8 | CCCACCCGCAAAACTGTAGGTGCCGCGGAGGAGCGGCCGCACCCGTTCTA GCCCGAAAGGGC (Sacll and Notl) |
| DRS-r | 9 | GCCCTTTCGGGCTAGAACGGGTGCGGCCGCTCCTCCGCGGCACCTACAGTT TTGCGGGTGGG (Sacll and Notl) |
| Apal-f | 10 | CCGTGTCGAAGGCTATCTCTGTAC |
| R1-Kpnl-r | 11 | ACGGAATTAATTCGAGCTCGGTACCCGTCGACCTCGATCCGGATATAGTTCC TCCTT (Kpnl and Sall) |
| R1$_{900}$-f | 12 | GGATTGATACCGAACTACACGTGCG |
| R1$_{1272}$M-r | 13 | TATTGGCGCGCACTCACTTCTGGTA (Bsshll and point mutation) |
| RepA-Dir | 14 | ACGTTAGCTAGCGATGTCTGGGAGAAAATTACACATGACAGC (Nhel) |
| RepA-Rev | 15 | TAACGTCTCGAGTCACTTCCGGTTGTTGGAAGGCTG (Xhol) |
| b-TAR-f | 16 | GGCCGCACTCGAGGCTCGTGTAGCTCATTAGCTCCGAGCGGTCACCGC (Xhol and Bstell) |
| b-TAR-r | 17 | GGCCGCGGTGACCGCTCGGAGCTAATGAGCTACACGAGCCTCGAGTGC (Xhol and Bstell) |
| B2-Dir | 18 | ACGTTAGCTAGCCCAAGCAAACTCGCGCTAATCCAG (Nhel) |
| B2-Rev | 19 | TAACGTCTCGAGCTACAGTTTTGCGGGTGGGGG (Xhol) |
| 6L1Δ4 | 20 | CGCGCCTAAGCGGCCGCG (Notl) |
| 6L1Δ4-inv | 21 | GGATTCGCCGGCGCAGCT (Notl) |
| Tat-dir | 22 | ACTGCGCGCCGTTTGTTTCATGACAAAAGCC (Bsshll) |
| Tat-rev | 23 | AGTGCGGCCGCTTACTGCTTTGATAGAGAAGCTTG (Notl) |
| R1-120 | 24 | GCACCCAGATACGGTTGCAATCCCGAC |
| AZ15-for | 25 | GCATGCATCTCAATTAGTCAGCAACCAGGATC |
| R1-90rev | 26 | CAATTCAGTTCGGGTGATCTGGTGTTCTCC |
| AZ-9rev | 27 | TTCGCAGTCCAGTGCTTGAGTTTGG |
| AZ-5rev | 28 | GCCCTTTCGGGCTAGAACGGG |
| R3-2809rev | 29 | GGTGCGTCTTGGTAGCTCATTCCCATG |
| R1-234for | 30 | CGAAGACCCCGATAGAGACACGTTTC |

The invention claimed is:

1. A modified nodavirus RNA1 molecule which includes a heterologous insertion downstream of the replicase ORF of said RNA1.

2. The RNA1 molecule of claim 1, wherein the heterologous insertion is also downstream of the B2 ORF of said RNA1.

3. The RNA1 molecule of claim 1, wherein the heterologous insertion is more than 5 nucleotides upstream of the 3' end of said RNA1.

4. The RNA1 molecule of claim 1, wherein the heterologous insertion comprises a protein-coding region.

5. The RNA1 molecule of claim 1, wherein said RNA1 comprises a sequence that can specifically interact with a protein sequence.

6. A VLP containing the RNA1 molecule of claim 1.

7. A single-stranded nucleic acid complementary to the RNA1 of claim 1.

8. A single-stranded nucleic acid comprising a sequence complementary to the RNA1 of claim 1.

9. A process for producing the RNA1 of claim 1, comprising the steps of: (a) obtaining nucleic acid comprising or encoding a nodavirus RNA1 sequence, and (b) inserting a heterologous sequence downstream of the replicase ORF within said RNA1 sequence.

10. The RNA1 molecule of claim 2, wherein the heterologous insertion is more than 5 nucleotides downstream of the replicase and B2 ORFs.

11. The RNA1 molecule of claim 4, wherein the heterologous insertion comprises an IRES upstream of the protein-coding region.

12. The RNA1 molecule of claim 5, wherein the sequence that can specifically interact with a protein sequence is a TAR sequence.

13. The RNA1 molecule of claim 12, wherein the TAR sequence is within the heterologous insertion.

14. The VLP of claim 6, wherein the VLP is a papillomavirus VLP.

15. A process for producing the VLP of claim 6, comprising the steps of: transfecting a cell with a single-stranded nucleic acid complementary to a modified nodavirus RNA1 molecule which comprises a heterologous insertion downstream of the replicase ORF of said RNA1; transfecting a cell with nucleic acid encoding a VLP capsid protein, optionally modified to include a motif specific for modified RNA1; and purifying VLPs from the cell.

16. A process for delivering a nucleic acid sequence of interest to a cell, comprising the step of introducing the VLP of claim 6 into said cell, wherein said nucleic acid sequence of interest is the modified RNA1 molecule contained in said VLP.

17. A process for delivering a nucleic acid sequence to a cell, comprising the step of introducing the VLP of claim 6 into said cell.

18. The VLP of claim 14, wherein the VLP comprises an L1 capsid protein comprising an insertion of a tat sequence, and the heterologous insertion of the modified nodavirus RNA1 molecule comprises an IRES upstream of a protein-coding region.

19. The VLP of claim 14, wherein the VLP comprises an L1 capsid protein comprising an insertion of a tat sequence, and the heterologous insertion of the modified nodavirus RNA1 molecule comprises a TAR sequence.

20. The VLP of claim 19, wherein the tat and TAR are from HIV or BIV.

21. A single-stranded nucleic acid complementary to the nucleic acid of claim 7.

22. A double-stranded nucleic acid, in which one of the strands is the single-stranded nucleic acid of claim 7.

23. A double-stranded nucleic acid, in which one of the strands is the single-stranded nucleic acid of claim 8.

24. The process of claim 9, wherein step (b) comprises inserting a heterologous sequence downstream of the replicase and B2 ORFs within said RNA1 sequence.

25. An RNA comprising a RNA1 sequence from a nodavirus, wherein the RNA1 sequence contains a heterologous insertion downstream of its replicase ORF.

26. The RNA of claim 25, wherein the heterologous insertion is downstream of the B2 ORF.

27. A modified nodavirus RNA1 molecule that comprises a heterologous insertion that comprises a protein-coding region, wherein the heterologous insertion is more than 5 nucleotides downstream of the replicase ORF and the B2 ORF of said RNA1 and is more than 5 nucleotides upstream of the 3' end of said RNA1.

28. The RNA1 molecule of claim 27, wherein the heterologous insertion comprises an IRES upstream of the protein-coding region.

29. The RNA1 molecule of claim 27, wherein said RNA1 comprises a sequence that can specifically interact with a protein sequence.

30. A VLP containing the RNA1 molecule of claim 27.

31. A single-stranded nucleic acid complementary to the RNA1 of claim 27.

32. A single-stranded nucleic acid comprising a sequence complementary to the RNA1 of claim 27.

33. A process for producing the RNA1 of claim 27, comprising the steps of: (a) obtaining nucleic acid comprising or encoding a nodavirus RNA1 sequence, and (b) inserting a heterologous sequence downstream of the replicase ORF within said RNA1 sequence.

34. The RNA1 molecule of claim 29, wherein the sequence that can specifically interact with the protein sequence is a TAR sequence.

35. The RNA1 molecule of claim 34, wherein the TAR sequence is within the heterologous insertion.

36. The VLP of claim 30, wherein the VLP is a papillomavirus VLP.

37. A process for producing the VLP of claim 30, comprising the steps of: transfecting a cell with a single-stranded nucleic acid complementary to a modified nodavirus RNA1 molecule that comprises a heterologous insertion that comprises a protein-coding region, wherein the heterologous insertion is more than 5 nucleotides downstream of the replicase ORF and the B2 ORF of said RNA1 and is more than 5 nucleotides upstream of the 3' end of said RNA1; transfecting a cell with nucleic acid encoding a VLP capsid protein, optionally modified to include a motif specific for modified RNA1; and purifying VLPs from the cell.

38. A process for delivering a nucleic acid sequence of interest to a cell, comprising the step of introducing the VLP of claim 30 into said cell, wherein said nucleic acid sequence of interest is the modified RNA1 molecule contained in said VLP.

39. A process for delivering a nucleic acid sequence to a cell, comprising the step of introducing the VLP of claim 30 into said cell.

40. The VLP of claim 36, wherein the VLP comprises an L1 capsid protein comprising an insertion of a tat sequence, and the heterologous insertion of the modified nodavirus RNA1 molecule comprises an IRES upstream of a protein-coding region.

41. The VLP of claim 36, wherein the VLP comprises an L1 capsid protein comprising an insertion of a tat sequence, and the heterologous insertion of the modified nodavirus RNA1 molecule comprises a TAR sequence.

42. The VLP of claim 41, wherein the tat and TAR are from HIV or BIV.

43. A double-stranded nucleic acid, in which one of the strands is the single-stranded nucleic acid of claim 31.

44. A double nucleic acid, in which one of the strands is the single-stranded nucleic acid of claim 32.

45. The process of claim 33, wherein step (b) comprises inserting a heterologous sequence downstream of the replicase and B2 ORFs within said RNA1 sequence.

46. The process of claim 39, performed in vitro.

47. The process of claim 39, performed in vivo.

48. A modified nodavirus RNA1 molecule comprising a heterologous insertion downstream of the replicase ORF of said RNA1, wherein said heterologous insertion is situated between the last nucleotide of the replicase ORF of said RNA1 and the last nucleotide of the RNA1 molecule.

49. An RNA comprising a RNA1 sequence from a nodavirus, wherein the RNA1 sequence contains a heterologous insertion downstream of its replicase ORF, wherein the heterologous insertion is situated between the last nucleotide of the replicase ORF of said RNA1 and the last nucleotide of the RNA1 sequence.

* * * * *